(12) United States Patent
Vaidyanathan et al.

(10) Patent No.: US 11,896,440 B2
(45) Date of Patent: Feb. 13, 2024

(54) MEDICAL DELIVERY SYSTEM

(71) Applicant: Medtronic, Inc., Minneapolis, MN (US)

(72) Inventors: Janardan Vaidyanathan, Thane (IN); Charles T. Graves, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 408 days.

(21) Appl. No.: 17/106,590

(22) Filed: Nov. 30, 2020

(65) Prior Publication Data
US 2022/0168063 A1    Jun. 2, 2022

(51) Int. Cl.
*A61B 90/10*    (2016.01)
*A61B 34/30*    (2016.01)
*A61B 17/34*    (2006.01)

(52) U.S. Cl.
CPC .............. *A61B 90/10* (2016.02); *A61B 34/30* (2016.02); *A61B 17/3468* (2013.01); *A61B 2034/301* (2016.02)

(58) Field of Classification Search
CPC ..... A61B 90/10; A61B 90/11; A61B 17/3468; A61B 34/30; A61B 2034/301; A61B 17/3421; A61B 2017/347; A61M 2210/0687; A61M 2210/0693; A61M 5/14276; A61N 1/0534; A61N 1/0529; A61N 1/0539; A61N 1/3605
See application file for complete search history.

(56) References Cited

U.S. PATENT DOCUMENTS

| | | | |
|---|---|---|---|
| 7,867,242 B2 | 1/2011 | Solar et al. | |
| 7,879,045 B2 | 2/2011 | Gielen et al. | |
| 8,845,655 B2 | 9/2014 | Henderson et al. | |
| 10,098,658 B2 | 10/2018 | Nelson | |
| 10,548,630 B2* | 2/2020 | Swaney | A61B 34/10 |
| 2006/0190054 A1* | 8/2006 | Malinowski | A61B 90/11 |
| | | | 607/45 |

(Continued)

OTHER PUBLICATIONS

Dembek et al., "Directional DBS Leads Show Large Deviations from their Intended Implantation Orientation," Parkinsonism and Related Disorders, vol. 67, Oct. 2019, pp. 117-121.

(Continued)

*Primary Examiner* — Timothy J Neal
*Assistant Examiner* — James R McGinnity
(74) *Attorney, Agent, or Firm* — Shumaker & Sieffert, P.A.

(57) ABSTRACT

A medical delivery system including a carrier and a lead delivery device. The carrier defines a carrier body configured to engage a stereotactic system (or a similar pointing device with or without navigation/robotic assistance). The carrier defines a carrier channel configured to engage the lead delivery device and impart a torque to a portion of the lead delivery device. The lead delivery device and carrier are configured to cause the imparted torque to cause a cannula of the lead delivery device to rotate about a longitudinal axis of the lead delivery device. The cannula is configured to cause a rotation of an implantable lead within the cannula when the cannula is caused to rotate. The cannula is configured to translate substantially parallel to the longitudinal axis relative to the implantable lead.

20 Claims, 9 Drawing Sheets

(56) References Cited

U.S. PATENT DOCUMENTS

2008/0275466 A1* 11/2008 Skakoon ............... A61B 90/11
                                                  604/116
2009/0143764 A1   6/2009  Nelson
2009/0187149 A1   7/2009  Nelson
2009/0264899 A1   10/2009 Appenrodt et al.

OTHER PUBLICATIONS

"Elekta MicroDrive™," Stereotactic Neurosurgery, Jun. 2006, 4 pp.
"Leksell® Coordinate Frame G," Stereotactic Neurosurgery, Jun. 2006, 4 pp.
"Leksell® Multi Purpose Stereotactic Arc," Stereotactic Neurosurgery, Jun. 2006, 4 pp.
1 Extended Search Report from counterpart European Application No. 21211232.0 dated Apr. 26, 2022, 8 pp.

* cited by examiner

MEDICAL DELIVERY SYSTEM

TECHNICAL FIELD

This disclosure is related to medical systems for the delivery of implantable leads.

BACKGROUND

Various types of medical delivery systems are utilized for implantation of medical leads. Such implantable leads may be adapted to allow medical devices to monitor (acute or chronically) or treat conditions or functions relating to heart, muscle, nerve, brain, stomach, endocrine organs or other organs and their related functions. Implantable leads include electrodes such as ring electrodes, segmented low- or high-resolution electrodes in a radial/array/matrix arrangement, etc. and/or other elements for physiological sensing and/or therapy delivery. Medical delivery systems allow the implantable leads to be positioned at one or more target locations for those functions, while the medical devices electrically coupled to those electrodes via the leads may be at different locations.

In some examples, medical delivery systems may position an implantable lead in the brain of a patient to treat a variety of medical conditions, including the relief of chronic pain (e.g., via electrical stimulation of the brain) and/or the treatment of movement disorders, epilepsy, psychiatric disorders, headaches, eating, hearing, vision disorders, and others. To accurately place the device (location and orientation) and avoid unintended injury to eloquent areas of the brain, clinicians may use stereotactic apparatus (or a similar pointing/guiding systems) to determine coordinates within the brain describing a target site. The stereotactic apparatus may assist in guiding surgical or other instruments (e.g., catheters and electrical leads) to the target site.

SUMMARY

In one example, a medical delivery system includes a lead delivery device defining a longitudinal axis and a lumen, wherein the lead delivery device comprises: a stereotactic collar defining a collar access at a proximal end of the lead delivery device; a cannula attached to the stereotactic collar and defining a distal opening at a distal end of the lead delivery device, wherein the lumen extends from the collar access to the distal opening; and an implantable lead within the lumen, wherein the cannula is configured to rotate the implantable lead around the longitudinal axis when the cannula rotates around the longitudinal axis, and wherein the cannula is configured to translate substantially parallel to the longitudinal axis relative to the implantable lead; and a carrier configured to engage the lead delivery device, wherein the carrier defines a carrier body, and wherein the carrier comprises: a drive mechanism configured to impart a torque to the lead delivery device to cause the cannula to rotate around the longitudinal axis relative to the carrier body when the carrier engages the lead delivery device.

In another example, a medical delivery system includes a lead delivery device having a proximal end and a distal end defining a longitudinal axis and a lumen, wherein the lead delivery device comprises: a stereotactic collar defining a collar access at a proximal end of the lead delivery device; a cannula attached to the stereotactic collar and defining a distal opening at a distal end of the lead delivery device, wherein the lumen extends from the collar access to the distal opening; and an implantable lead within the lumen, wherein the cannula is configured to rotate the implantable lead around the longitudinal axis when the cannula rotates around the longitudinal axis, and wherein the cannula is configured to translate substantially parallel to the longitudinal axis relative to the implantable lead; and a carrier configured to engage the lead delivery device, wherein the carrier defines a carrier body, wherein the carrier comprises: a drive mechanism configured to receive a torque and impart a portion of the torque to the lead delivery device to cause the cannula to rotate around the longitudinal axis relative to the carrier body when the carrier engages the lead delivery device, and wherein the drive mechanism comprises: a turn knob configured to receive the torque, wherein the turn knob is accessible from an exterior surface of the carrier; and a turn enable having a first position and a second position, wherein the turn enable is configured to allow the drive mechanism to impart the portion of the torque to the lead delivery device in the first position and configured to prevent the prevent the drive mechanism from imparting the portion of the torque to the lead delivery device in the second position.

In another example, a method includes imparting a torque from a drive mechanism of a carrier to a lead delivery device positioned in a carrier channel defined by the carrier; causing a cannula attached to a stereotactic collar of the lead delivery device to rotate around a longitudinal axis of the lead delivery device using the imparted torque; and causing an implantable lead within a lumen of the lead delivery device to rotate around the longitudinal axis of the lead delivery device using the rotation of the cannula.

The details of one or more examples are set forth in the accompanying drawings and the description below. Other features, objects, and advantages will be apparent from the description and drawings, and from the claims.

DETAILED DESCRIPTION

Figure 1:
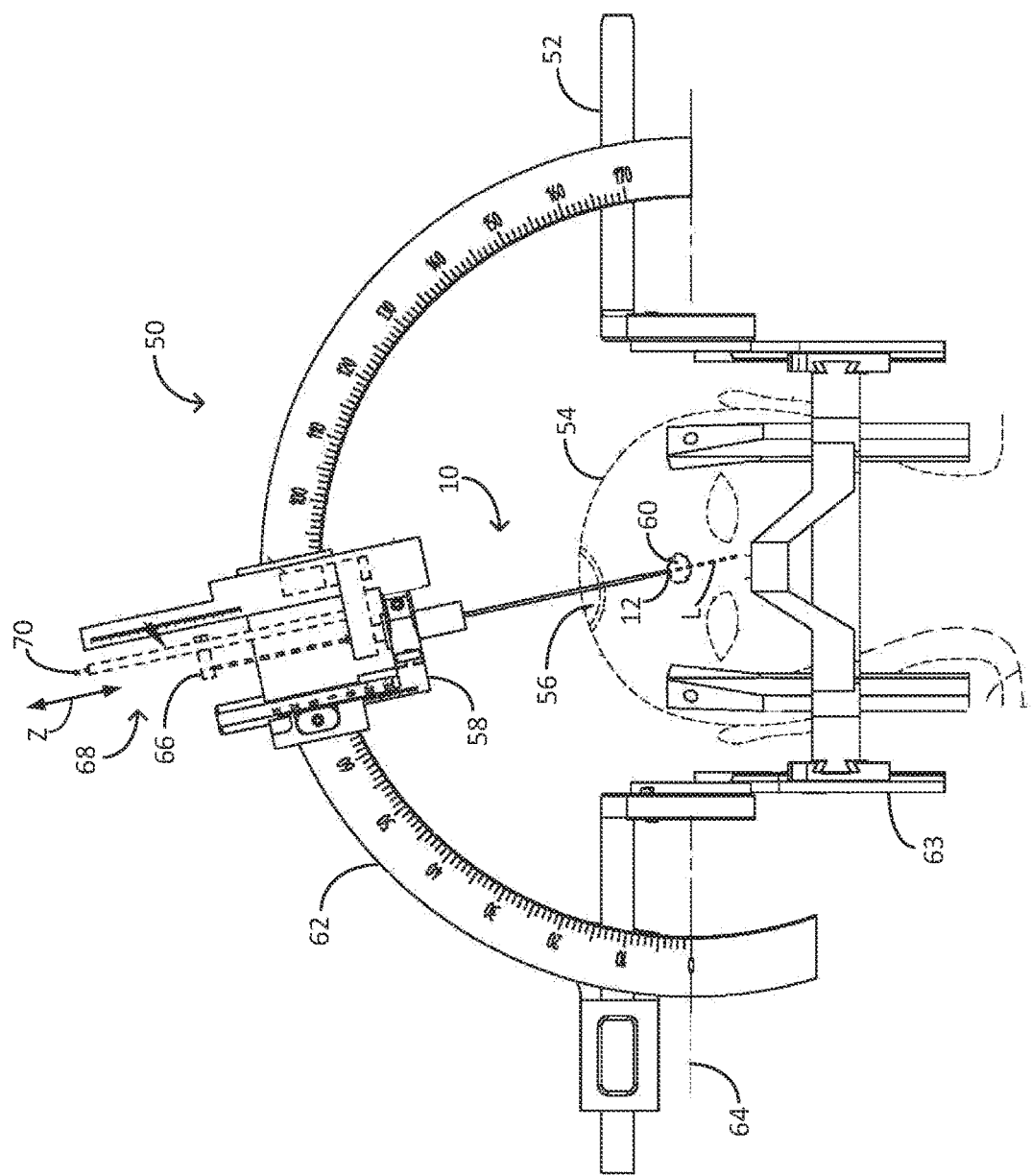
FIG. 1 is a conceptual diagram illustrating an example stereotactic system and medical delivery system.

This disclosure describes a medical delivery system configured to deliver an implantable lead to a target site within a patient. The medical delivery system may deliver the implantable lead to a target site within the brain of a patient for Deep Brain Stimulation (DBS) or another purpose. In examples, the implantable lead includes one or more electrodes configured to deliver stimulation therapy to the patient. The one or more electrodes may include, for example, one or more ring electrodes, segmented low- or high-resolution electrodes in a radial/array/matrix arrangement, etc., and others. For example, the implantable lead may include one or more electrodes configured to deliver stimulation therapy to the brain of a patient to treat a variety of medical conditions, including the relief of chronic pain and/or the treatment of movement disorders, epilepsy, psychiatric disorders, headaches, eating, hearing, vision disorders, and others. A relative effectiveness of the stimulation may be dependent on the positioning and/or orientation of the electrode relative to the target site. For example, the electrode may be a substantially directional electrode (e.g, a segmented ring electrode) configured to exhibit a directionality dependent on a radial orientation of the implantable lead (e.g, for current fractionalization). In certain cases, once the directional lead is delivered at or near the target site, it may be necessary to rotate the implantable lead about a lead axis to cause a rotation of the electrode about the lead axis, in order to vary the direction and/or orientation of the electrode relative to the target site and evaluate the effectiveness of the direction (e.g, pointing to the source of a biomarker).

The medical delivery system disclosed may be configured to utilize an implantable lead to position a directional electrode at or near a target site, and configured to provide for rotation of the implantable lead and the directional electrode about a lead axis, such that the positioning of the directional electrode relative to the target site may be evaluated. The medical delivery system is configured to allow a clinician to cause a torque on the implantable lead and/or a lead delivery device which causes a substantially uniform rotation of the implantable lead, in order to substantially avoid twisting or other rotational and/or torsional variations along the implantable lead which may impact the position and/or orientation of the directional electrode achieved. The medical delivery system may be configured to provide an indication of the radial position of the implantable lead and directional electrode relative to a stereotactic system, in order to provide for recording and/or stimulation and repeatability of the various relative orientations of the directional electrode evaluated. The lead delivery device may include a stereotactic collar at a proximal end and a cannula extending distally from the stereotactic collar to impart the torque on the implantable lead.

In examples, the medical delivery system is configured to engage a stereotactic system (e.g., a rigid stereotactic frame, frameless delivery devices, pointing/aiming guidance systems, etc.) configured to provide positional reference relative to a patient. The medical delivery system is configured to provide for rotation of an implantable lead around an axis relative to the stereotactic system (or a similar reference frame encompassing the target). The medical delivery system is configured to indicate the angle of rotation and the translation of the implantable lead relative to the engaged stereotactic system. The medical delivery system may allow for translation of the implantable medical lead along a longitudinal axis and rotation of the implantable medical lead around the longitudinal axis, to provide for graded targeting.

The implantable lead may include one or more electrodes configured to deliver stimulation therapy or acutely/chronically sense biomarkers in a patient. For example, the implantable lead may include one or more electrodes configured to deliver stimulation therapy to the brain of a patient to treat a variety of medical conditions, including the relief of chronic pain (e.g., via electrical stimulation of the brain) and/or the treatment of movement disorders, epilepsy, psychiatric disorders, headaches, eating, hearing, vision disorders, and others.

The medical delivery system is configured to allow a clinician to cause rotation of the implantable lead within a patient (e.g., rotation about a longitudinal axis of the implantable lead) by imparting a torque on a turn knob of the medical delivery system. In examples, the medical delivery system may be utilized to position an electrode on the implantable lead at a target site within the brain of a patient. The medical delivery system may be used to identify an effective orientation of the electrode by causing the rotation of the implantable lead in the vicinity of the target site. The medical delivery system may be used to verify the effective orientation by recording signals and confirming detection of a biomarker or causing the electrode to record a sensing signal and/or issue a stimulation in the effective orientation (e.g., test stimulation). Following the identification and verification, the medical delivery system may be used to implant the lead by withdrawing a cannula of the medical delivery system from the patient while the oriented implantable lead remains intact (for fixation thereafter by a locking/anchoring mechanism) in the patient. Further, the medical delivery system may be configured to provide an indication of an angle of rotation of the implantable lead. Thus, the medical delivery system may be utilized to record an orientation of the implantable lead relative to the stereotactic system.

The medical delivery system includes a lead delivery device and a carrier configured to engage the lead delivery device. In examples, a body of the carrier ("carrier body") defines a carrier channel, and some portion of the lead delivery device is configured to insert into the carrier channel. The lead delivery device may include a stereotactic collar at a proximal end and a cannula extending distally from the stereotactic collar. The stereotactic collar is configured to provide a positional reference of the lead delivery device relative to the carrier. The cannula is configured to rotate around a longitudinal axis relative to the carrier. The cannula is configured to rotate an implantable lead within a lumen of the cannula when the cannula rotates around the longitudinal axis. In examples, the carrier is configured to engage a stereotactic system such that the carrier body of the carrier is stationary with respect to the stereotactic system.

In examples, the carrier includes a drive mechanism configured to cause rotation of the cannula relative to the carrier body. The drive mechanism may be configured to cause rotation of the cannula as the carrier engages a stereotactic system, such that the drive mechanism causes rotation of the cannula relative to the stereotactic system. The drive mechanism may be configured to receive an input torque from a turn knob and transmit a rotational torque to the lead delivery device using the input torque, in order to cause the cannula (and the implantable lead within the cannula, and/or the electrode) to rotate around the longitudinal axis relative to the carrier body. The drive mechanism may provide an indication of an angle of rotation of the cannula with respect to the carrier body. Hence, when the carrier is engaged with the drive lock ring of the stereotactic collar and further engaged with a stereotactic frame, the medical delivery system may be configured to indicate an angle of rotation of an implantable lead within the lumen relative to the carrier body and/or stereotactic frame.

In examples, the drive mechanism includes a turn enable control that may be adjustable between at least a first position and a second position. The turn enable control may be configured to allow the drive mechanism to impart the rotational torque to the lead delivery device in the first position and configured to prevent the drive mechanism from imparting the rotational torque to the lead delivery device in the second position. The turn enable control may be adjustable by a clinician, such that rotation of the cannula and implantable lead may be effectively locked and unlocked as the clinician establishes various rotational positions of the implantable lead relative to a reference system (e.g., a stereotactic frame). Rotation can be in steps or adjustable on a continuous scale covering a specific range or encompassing the entire range of radial movement available.

The lead delivery device may be configured to translate the cannula in a direction substantially parallel to the longitudinal axis of the implantable lead. In examples, the medical delivery system is configured to translate the cannula substantially parallel to the longitudinal axis while the implantable lead is maintained substantially stationary, such that cannula translates relative to the implantable lead. In examples, the medical delivery system is configured to translate the implantable medical lead substantially parallel to the longitudinal axis while the cannula is maintained substantially stationary, such that the implantable lead translates relative to cannula. The medical delivery system may be configured to provide an indication of an amount the cannula has translated relative to the implantable lead, or vice-versa. Hence, when the carrier is engaged with the stereotactic collar and further engaged with a stereotactic system, the medical delivery system may be configured to indicate the position of the implantable lead relative to the stereotactic system.

The implantable lead may include a stylet configured to translate the implantable lead relative to the cannula. The stylet may be configured to translate the implantable lead relative to the cannula when the stylet translates relative to the stereotactic collar. In examples, the stereotactic collar includes a stylet fixation mechanism configured to limit and/or substantially cease the translation of the stylet relative to the stereotactic collar. The stylet fixation mechanism may be configured to mechanically engage the stylet at defined locations along the stylet, such that the stylet fixation mechanism substantially indexes the translation of the stylet (and the implantable lead) relative to the stereotactic collar. The mechanical engagement at defined locations along the stylet may be utilized to define a position of the implantable lead relative to the stereotactic collar and/or cannula. Hence, the stylet fixation mechanism may be configured to indicate the amount the cannula has translated substantially parallel to the longitudinal axis relative to the implantable lead.

In examples, the stereotactic collar includes a drive lock ring and a drive turn ring attached to the drive lock ring, with the drive turn ring configured to rotate around the longitudinal axis of the lead delivery device relative to the drive lock ring. The cannula may be attached to the drive turn ring such that rotation of the drive turn ring causes rotation of the cannula. The drive mechanism may be configured to impart a rotational torque to the drive turn ring and/or cannula to cause rotation of the drive turn ring and cannula. The carrier may be configured to mechanically engage the drive lock ring such that the drive lock ring remains substantially stationary relative to the carrier body as the drive mechanism rotates the drive turn ring and cannula relative to the carrier body.

FIG. 1 is a conceptual diagram illustrating an example medical delivery system 10. As illustrated in FIG. 1, medical delivery system 10 may optionally be utilized with a separate surgical apparatus, e.g., a stereotactic system 50. The stereotactic system 50 may include a stereotactic frame 52 fixedly attached to the head or skull 54 of a patient and positioned relative to a burr hole 56 formed through the skull. While illustrated in FIG. 1 as using the stereotactic system 50, medical delivery system 10 may be used without these items, or may be used with other apparatus, pointing or aiming devices with or without tool holders, translocation methods, guidance, and/or placement systems in other examples. Stereotactic frame 52 may be, for example, a rigid stereotactic frame, a mini-frame, a frameless delivery device, image/MRI guided/navigated system, patient specific 3D printed device, or some other system configured to provide positional reference relative to a patient.

Stereotactic frame 52 includes a mount (also called as instrument stop/guide holder) 58 configured to support medical delivery system 10. Stereotactic frame 52 is configured such that mount 58 may be positioned in three dimensions relative (e.g., pointing) to a target site 60 within a skull 54 of a patient. In examples, stereotactic frame 52 includes a substantially semicircular arc 62 defining the surface of a hemi-sphere along which mount 58 may be adjustably positioned. Semicircular arc 62 may be user adjustable, e.g., pivot about a transverse pivot axis 64 relative to arc supports 63 of stereotactic frame 52. Positioning of mount 58 along semicircular arc 62 and rotation of semicircular arc 62 around transverse pivot axis 64 allows mount 58 to be positioned in specific positions (along specific trajectories) around skull 54 (traversing a cone as an instance). Similar approaches for translocation in pointing/guidance devices could include an inverted cone, double intersecting cone or a cylinder within a ring etc. For example, mount 58 may be positioned on stereotactic frame 52 such that mount 58 is generally aligned with target site 60 within skull 54 based on a surgical plan. Once located relative to burr hole 56 and target site 60, mount 58 may be generally fixed to restrict movement of mount 58 along semicircular arc 62 and about the axis 64, by fasteners, thumbwheels, thumbscrews or the like. Burr hole 56 may be formed during a surgical procedure and based upon the previously determined target site 60 and an associated entry point. Medical delivery system 10 may be configured to mechanically couple with mount 58 such that a position of some portion of medical delivery system 10 (e.g., a carrier) relative to target site 60 may be determined based on the position of mount 58.

Medical delivery system 10 may be may configured to mechanically couple with mount 58 using any appropriate method or device suitable to reference the position of medical delivery system 10 to the position of mount 58. In examples, medical delivery system 10 is configured to engage a carrier platform 66 mechanically coupled to mount 58. Carrier platform 66 may be configured to translate substantially parallel to or substantially coincident with an axis Z relative to mount 58 (e.g., along a chosen trajectory among a plurality of parallel trajectories). In some examples, translation of carrier platform 66 (and medical delivery system 10 when engaged) relative to mount 58 may be at least partially automated with the use of an optional drive member, such as microdrive 68 (e.g., operated manually or using an electric motor). Microdrive 68 may be configured to selectively translate carrier platform 66 along a drive screw 70 to selectively advance or withdraw carrier platform 66 and medical delivery system 10 in a direction of the axis Z relative to mount 58.

Carrier platform 66 and/or medical delivery system 10 may be configured such that, when medical delivery system 10 engages carrier platform 66, a longitudinal axis L of medical delivery system 10 is substantially parallel and/or substantially coincident with the axis Z. Hence, translation of carrier platform 66 (e.g., by rotation of the screw 70) along the axis Z may cause translation of medical delivery system 10 in either direction along the longitudinal axis L of medical delivery system 10. For example, translation of carrier platform 66 may cause translation of distal end 12 of medical delivery system 10 along longitudinal axis L. Hence, translation of carrier platform 66 along the axis Z may cause translation of an implantable lead within medical delivery system 10 toward or away from target site 60 within skull 54. Translation of carrier platform 66 may be utilized to position an electrode of the implantable lead within the vicinity of target site 60.

Further, medical delivery system 10 is configured to rotate around longitudinal axis L relative to some portion of stereotactic frame 52 (e.g., mount 58 and/or carrier platform 66) when medical delivery system 10 is mechanically coupled with mount 58. In examples, medical delivery system 10 includes a drive mechanism configured to cause the rotation of medical delivery system 10. Medical delivery system 10 may be configured to indicate an angle of rotation of medical delivery system 10 (e.g., distal end 12) relative to a portion of stereotactic frame 52 (e.g., mount 58 and/or carrier platform 66). In examples, medical delivery system 10 includes an implantable lead configured to deliver stimulation therapy to target site 60, and the angle of rotation of medical delivery system 10 is indicative of the rotational orientation of the implantable lead, and/or an electrode in the implantable lead. As such, rotation of medical delivery system 10 may result in rotation of the implantable lead and/or the electrode (e.g., to facilitate fractionalization of delivered therapy in a certain direction).

Hence, medical delivery system 10 is configured to mechanically couple with mount 58 (e.g., carrier platform 66) such that positioning of mount 58 relative to target site 60 allows access to target site 60 by medical delivery system 10. A position and orientation of medical delivery system 10 relative to target site 60 may be substantially determined based on the position and orientation of mount 58 on stereotactic frame 52, as well as the translation of medical delivery system 10 along longitudinal axis L relative to stereotactic frame 52 and the rotation of medical delivery system 10 around longitudinal axis L relative to stereotactic frame 52. A practitioner (e.g., a surgeon, a physician's assistance, a nurse, etc.) may cause medical delivery system 10 to translate along and/or rotate around longitudinal axis L in order to establish a specific position and orientation of an implantable lead relative to target site 60. For example, the practitioner may cause medical delivery system 10 to translate along and rotate around longitudinal axis L in order to evaluate various positions and orientations of an implantable lead within medical delivery system 10 relative to target site 60.

Figure 2:
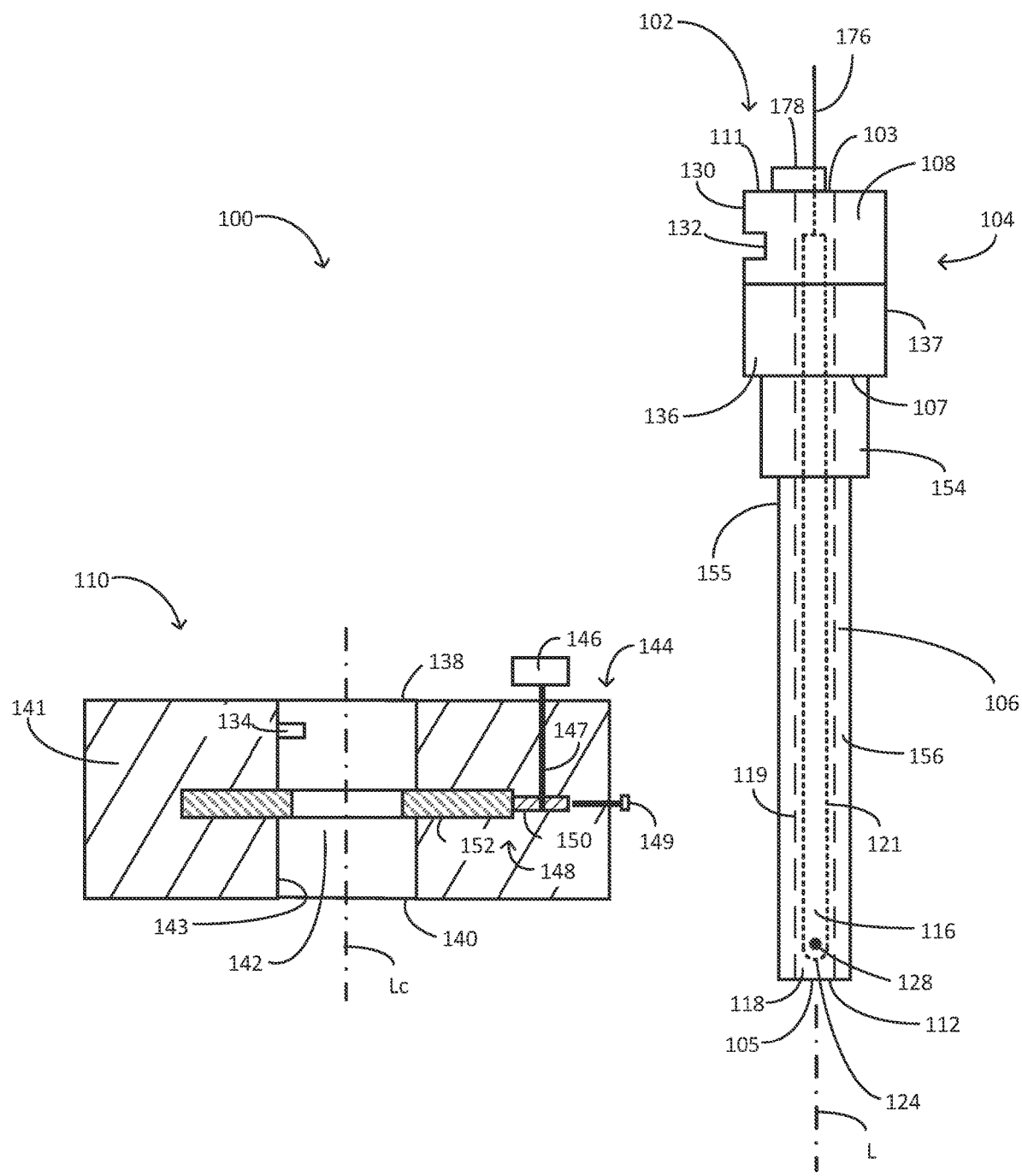
FIG. 2 is a plan view with selected cross-sections illustrating an example medical delivery system.

FIG. 2 is a conceptual diagram illustrating a portion of a medical delivery system 100. Medical delivery system 100 includes a carrier 110, and includes a lead delivery device 102 defining a longitudinal axis L. Medical delivery system 100 is an example of medical delivery system 10 (FIG. 1). Carrier 110 is shown in cross-section in FIG. 2, with a cutting plane taken parallel to the page.

Lead delivery device 102 defines a longitudinal axis L extending from a proximal end 111 of lead delivery device 102 ("device proximal end 111") to a distal end 112 of lead delivery device 102 ("device distal end 112"). Lead delivery device 102 includes a stereotactic collar 104 at device proximal end 111. A cannula 106 extends from stereotactic collar 104 to a distal end 112 of lead delivery device 102 ("device distal end 112"). Cannula 106 may be attached to stereotactic collar 104 at a proximal end 107 of cannula 106 ("cannula proximal end 107"). Stereotactic collar 104 defines a collar access 103 at device proximal end 111 and cannula 106 defines a distal opening 105 at device distal end 112. Lead delivery device 102 defines a lumen 118 extending from collar access 103 to distal opening 105. Longitudinal axis L may extend through lumen 118. In examples, longitudinal axis L extends through collar access 103 and distal opening 105. In examples, an exterior surface 130 of stereotactic collar 104 ("collar exterior surface 130") may have serrations configured to engage a thumb screw to cause fine translational movement of lead delivery device 102 along longitudinal axis L. The thumb screw may include a set of serrations configured to engage the serrations of exterior surface 130. The serrations of exterior surface 130 and/or the thumb screw may have any orientation relative to longitudinal axis L. In examples, the serrations of exterior surface 130 and/or the thumbscrew are substantially perpendicular or substantially parallel to longitudinal axis L.

An implantable lead 116 extends within lumen 118. Lumen 118 and implantable lead 116 are shown in hidden lines in FIG. 2. Lead delivery device 102 is configured such that when cannula 106 rotates around longitudinal axis L, the rotation of cannula 106 causes a rotation of implantable lead 116 around longitudinal axis L. Lead delivery device 102 is further configured such that cannula 106 may translate substantially parallel to longitudinal axis L relative to implantable lead 116. Lead delivery device 102 may be configured such that translation of cannula 106 relative to implantable lead 116 causes a translation of device distal end 112 and distal opening 105 relative to a distal end 124 of implantable lead 116 ("lead distal end 124"). Distal opening 105 may be configured to allow passage of lead distal end 124 through distal opening 105.

In examples, lead distal end 124 includes an electrode 128 configured to deliver therapy and/or stimulation to a target site (e.g., target site 60 (FIG. 1)) and/or sense a brain state/disease/symptom biomarker at the target site. Lead delivery device 102 may be configured to translate cannula 106 between a first position wherein cannula distal opening 105 is distal to electrode 128 to a second position wherein cannula distal opening 105 is proximal to electrode 128. In the second position, cannula 106 remains configured to rotate implantable lead 116 around the longitudinal axis when cannula 106 rotates around longitudinal axis L. Cannula 106 may be configured to rotate implantable lead 116 around the longitudinal axis L when cannula 106 rotates around the longitudinal axis with cannula distal opening 105 distal to, proximal to, and/or substantially even with electrode 128. Consequently, lead delivery device 102 may be configured to withdraw distal opening 105 proximal to electrode 128 to expose electrode 128, followed by rotation of cannula 106 to vary an orientation of electrode 128 within tissues in the vicinity of a target site (e.g., target site 60 (FIG.

1)). Additionally, when cannula 106 is in the second position, lead delivery device 102 may be configured to translate cannula 106 to the first position, and rotate cannula 106 in the first position to vary an orientation of electrode 128 within tissues in the vicinity of a target site (e.g., target site 60 (FIG. 1)).

In examples, cannula 106 may be caused to translate relative to implantable lead 116 by maintaining stereotactic collar 104 substantially stationary and causing implantable lead 116 to translate relative to stereotactic collar 104. In some examples, implantable lead 116 includes a stylet 176 configured to exert a force on implantable lead 116 substantially parallel to longitudinal axis L. Implantable lead 116 may be configured such that the force exerted by stylet 176 causes implantable lead 116 to translate substantially parallel to longitudinal axis L relative to stereotactic collar 104. In some examples, cannula 106 may be caused to translate relative to implantable lead 116 by translating stereotactic collar 104 substantially parallel to longitudinal axis L (e.g., using stereotactic system 50 (FIG. 1)) while maintaining implantable lead 116 substantially stationary. In examples, stylet 176 may be configured to impart a torque (e.g. a torque around longitudinal axis L) to implantable lead 116. Implantable lead 116 may be configured such that a translation and/or rotation of some portion of stylet 176 around longitudinal axis L causes a rotation of implantable lead 116 around longitudinal axis L. Lead delivery device 102 (e.g., stereotactic collar 104) may include a stylet fixation mechanism 178 configured to engage stylet 176 to control a motion of stylet 178 relative to stereotactic collar 104 and/or cannula 106.

In examples, cannula 106 is a substantially unitary body between cannula proximal end 107 and device distal end 112. Cannula 106 may define a substantially rigid body between cannula proximal end 107 and device distal end 112, such that a force exerted on device distal end 112 substantially parallel to longitudinal axis L is transmitted through cannula 106 to cannula proximal end 107, and vice-versa. In some examples, cannula 106 includes a proximal section 154 ("cannula proximal section 154") configured to translate relative to attached distal section 156 of cannula 106 ("cannula distal section 156"). Cannula proximal section 154 may be attached to stereotactic collar 104 and cannula distal section 156 may define device distal end 112. Cannula distal section 156 may be configured to translate along longitudinal axis L relative to cannula proximal section 154 to cause cannula 106 to translate relative to implantable lead 116. In examples, cannula distal section 156 is configured to telescope proximally and/or distally from cannula proximal section 154.

Carrier 110 comprises: a body 141 of carrier 110 ("carrier body 141") and a drive mechanism 144. Carrier 110 is configured to engage lead delivery device 102. In examples, carrier 110 defines a carrier channel 142 configured to receive a portion of lead delivery device 102 (e.g., stereotactic collar 104) when carrier 110 engages lead delivery device 102. When carrier 110 engages lead delivery device 102, drive mechanism 144 is configured to impart a rotational torque on lead delivery device 102 to cause cannula 106 to rotate around longitudinal axis L relative to carrier body 141. In examples, carrier body 141 defines an access port 138 and an outlet port 140, with carrier channel 142 extending between access port 138 and outlet port 140. A portion of lead delivery device 102 (e.g., stereotactic collar 104) may be configured to position within carrier channel 142 when carrier 110 engages lead delivery device 102.

In examples, carrier 110 defines a channel axis Lc extending through carrier channel 142. Carrier 110 may be configured to receive lead delivery device 102 in carrier channel 142 (e.g., via access port 138) and engage lead delivery device 102 (e.g., stereotactic collar 104) within carrier channel 142. Longitudinal axis L of lead delivery device 102 may extend through carrier channel 142 when carrier 110 engages lead delivery device 102. In examples, longitudinal axis L is substantially parallel to channel axis Lc when carrier 110 engages lead delivery device 102. Longitudinal axis L may be substantially coincident with channel axis Lc when carrier 110 engages lead delivery device 102. In examples, carrier 110 is configured such that, when medical delivery system 10 is mechanically coupled to stereotactic frame 52 (FIG. 1) and carrier channel 142 engages lead delivery device 102, longitudinal axis L of lead delivery device 102 is substantially parallel to the Z axis defined by stereotactic frame 52. The Z axis of stereotactic frame 52 may define a trajectory toward target site 60. In examples, longitudinal axis L is substantially coincident with the Z axis when medical delivery system 10 is mechanically coupled to stereotactic frame 52.

As illustrated by FIG. 2, in some examples carrier 110 and lead delivery device 102 are configured to be substantially separable and discrete portions of medical delivery system 100, however this is not required in all examples. In other examples, carrier 110 and lead delivery device 102 may be configured as substantially inseparable portions of medical delivery system 100.

Figure 3:
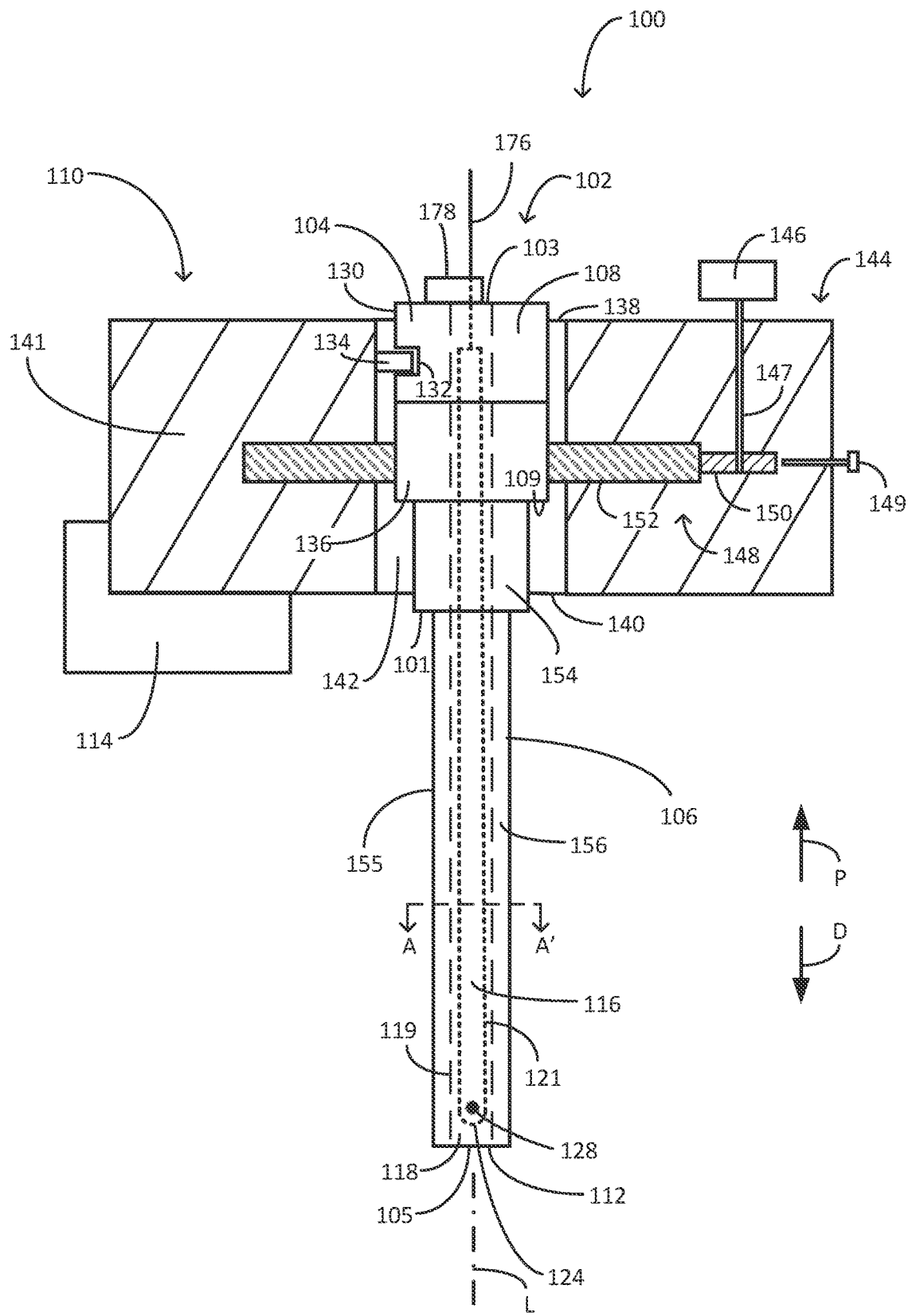
FIG. 3 is a plan view with selected cross-sections illustrating an example carrier engaging an example lead delivery device.

FIG. 3 is a conceptual diagram illustrating a plan view of medical delivery system 100 with carrier 110 engaging lead delivery device 102. Drive mechanism 144 is configured to impart a rotational torque on lead delivery device 102 to cause cannula 106 to rotate around longitudinal axis L relative to carrier body 141. Drive mechanism 144 may be configured to receive an input torque and impart the rotational torque on lead delivery device 102 (e.g., stereotactic collar 104 and/or cannula 106). In examples, drive mechanism 144 is configured to receive the input torque (e.g., from a clinician) via turn knob 146. In examples, drive mechanism 144 is configured to transmit the portion of the input torque to cause the rotational torque on driven gear 152.

Driven gear 152 is shown in cross-section in FIG. 2 and FIG. 3 with the cutting plane parallel to the page. Driven gear 152 may be configured to impart the rotational torque to lead delivery device 102 to cause cannula 106 to rotate around longitudinal axis L relative to carrier body 141. In examples, driven gear 152 is configured to mechanically engage collar exterior surface 130 of stereotactic collar 104 and/or an exterior surface 155 of cannula 106 ("cannula exterior surface 155"). Cannula 106 is configured to cause implantable lead 116 to rotate when drive mechanism 144 causes lead delivery device 102 (e.g., cannula 106) to rotate. Further, lead delivery device 102 is configured to translate cannula 106 along longitudinal axis L relative to implantable lead 116. For example, lead delivery device 102 is configured to translate cannula 106 in the proximal direction P such that device distal end 112 and distal opening 105 are proximal to lead distal end 124, in order to position electrode 128 distal to device distal end 112 and distal opening 105.

Hence, medical delivery system 100 may be configured such that, when carrier 110 engages lead delivery device 102, drive mechanism 144 may cause rotation of cannula 106 and implantable lead 116 around longitudinal axis L using turn knob 146. Electrode 128 may be distal to device distal end 112 and distal opening 105 during the rotation, such that a rotational orientation of electrode 128 in the vicinity of a target site (e.g., target site 60 (FIG. 1) may be evaluated. In examples, electrode 128 may be configured to sense/record biomarkers, deliver therapy and/or stimulation signals to target site 60. A clinician may cause medical delivery system 100 to vary the relative position of electrode 128 (e.g., by causing rotation of cannula 106) with respect to target site 60 in order to identify a biomarker, evaluate an effectiveness of stimulation and/or therapy delivered, or for other reasons. Medical delivery system 100 may define an angle of rotation corresponding to each relative orientation of electrode 128 evaluated. The defined angle of rotation and translation of each relative orientation of electrode 128 may be recorded, such that the clinician may repeat a relative orientation of electrode 128 deemed effective.

In examples, medical delivery system 100 is configured to couple with a platform 114 of a stereotactic system (e.g., frame 52 (FIG. 1)) to allow the position and angle of rotation of lead delivery device 102 to be determined with respect to the stereotactic system. Platform 114 may be, for example, mount 58, carrier platform 66, or some other portion of stereotactic frame 52 (FIG. 1). Medical delivery system 100 may be configured such that platform 114 substantially constrains at least carrier body 141 from motion around any/all/some stereotactic frame axes or along longitudinal axis L independent of platform 114. With platform 114 substantially constraining carrier body 141, and with cannula 106 and implantable lead 116 configured to rotate around longitudinal axis L relative to carrier body 141, medical delivery system 100 may be configured to define an angle of rotation of implantable lead 116 and electrode 128 relative to stereotactic frame 52 (FIG. 1). Hence, medical delivery system 100 may be configured to define a rotational orientation of implantable lead 116 and electrode 128 relative to a target site 60 within a patient.

As discussed, carrier 110 is configured to impart a rotational torque around longitudinal axis L to lead delivery device 102 to cause cannula 106 and implantable lead 116 to rotate around longitudinal axis L relative to carrier body 141. In examples, drive mechanism 144 includes a turn knob 146 configured to receive an input torque (e.g., from a clinician) and cause a rotational torque on lead delivery device 102 using the input torque. Turn knob 146 may be configured to transmit the input torque using torque member 147. Drive mechanism 144 may include a gear set 148 (e.g., driver gear 150 and driven gear 152) configured to transmit a portion of the input torque to lead delivery device 102. Drive mechanism 144 may further include a turn enable 149 configured to either allow or prevent transmission of the input torque by drive mechanism 144. In some examples, instead of or in additions to turn knob 146, drive mechanism 144 may include one or more devices and/or components configured to generate the input torque. For example, drive mechanism 144 may be configured to generate the input torque using a position motor such as a stepper motor or servomotor. The position motor may be a closed-loop servomechanism including a position encoder and/or rotary encoder. In examples, drive mechanism 144 is configured to generate an electric or magnetic field rotating around channel axis Lc, and some portion of lead delivery device 102 is configured to synchronously or asynchronously follow the rotating field.

Carrier 110 may be configured to substantially limit movement of stereotactic collar 104 relative to carrier body 141 in a direction substantially parallel to longitudinal axis L. Carrier 110 may be configured to mechanically engage collar exterior surface 130 to limit movement of stereotactic collar 104. In examples, one of carrier 110 or collar exterior surface 130 defines a protrusion and the other of carrier 110 or collar exterior surface 130 defines a recess configured to receive the protrusion, and carrier 110 substantially constrains stereotactic collar 104 when the recess receives the protrusion. For example, collar exterior surface 130 may define a recessed divot 132 configured to receive a protruding member 134 defined by carrier 110. In other examples, collar exterior surface 130 may define the protrusion and carrier 110 may define the recess. The protrusion may be adjustable (e.g., manually adjustable and/or spring-loaded) such that the protrusion may be caused to insert into the recess when the recess is sufficiently aligned with the protrusion (e.g., as carrier 110 receives lead delivery device 102 via access port 138). In some examples, medical delivery system 100 includes a collet configured to surround some portion of stereotactic collar 104 and expand or contract to cause carrier 110 to substantially constrain stereotactic collar 104 from translation along longitudinal axis L relative to carrier 110. The collet may be located within carrier channel 142 or elsewhere within medical delivery system 100.

In examples, stereotactic collar 104 includes a drive lock ring 108 and a drive turn ring 136. Drive turn ring 136 may be configured to rotate around longitudinal axis L relative to drive lock ring 108. Drive lock ring 108 and/or drive turn ring 136 may be configured such that drive lock ring 108 limits movement of drive turn ring 136 along longitudinal axis L relative to drive lock ring 108. For example, drive lock ring 108 and drive turn ring may be configured to form a rotary union whereby a torque around longitudinal axis L imparted to drive turn ring 136 causes drive turn ring 136 to rotate around longitudinal axis L relative to drive lock ring 108, while a force substantially parallel to longitudinal axis L exerted on drive turn ring 136 causes drive lock ring 108 to exert an equal and opposite reaction force on drive turn ring 136. Cannula 106 may extend from drive turn ring 136 and be configured such that a rotation of drive turn ring 136 around longitudinal axis L causes a rotation of cannula 106 around longitudinal axis L. In examples, carrier 110 is configured to mechanically engage drive lock ring 108 (e.g., using protruding member 134) such that drive lock ring 108 is substantially stationary with respect to carrier body 141.

In other examples, lead delivery device 102 may be configured to engage some portion of platform 114 to substantially limit movement of stereotactic collar 104 along longitudinal axis L relative to carrier body 141. For example, lead delivery device may define a bearing surface 109 on stereotactic collar 104, a bearing surface 101 on cannula 106, or a bearing surface located elsewhere configured to contact platform 114 and limit movement of lead delivery device 102 relative to carrier body 141 in at least the distal direction D. The bearing surface may be configured to slidably engage platform 114, such that, as the bearing surface constrains stereotactic collar 104 from movement along longitudinal axis L relative to platform 114, the bearing surface may rotate around longitudinal axis L relative to platform 114 (e.g., when stereotactic collar 104 and/or cannula 106 rotates relative to carrier body 141 and platform 114).

As discussed, drive mechanism 144 is configured to impart a torque on lead delivery device 102 when carrier 110 engages lead delivery device 102 (e.g., when lead delivery device is positioned within carrier channel 142). Lead delivery device 102 is configured such that the imparted torque causes cannula 106 to rotate relative to carrier body 141. Cannula 106 is configured to cause implantable lead 116 to rotate around longitudinal axis L when cannula 106 rotates around longitudinal axis L. In examples, drive mechanism 144 is configured to receive an input torque via turn knob 146 (e.g., from a clinician) in order to establish implantable lead 116 in a rotational orientation relative to carrier body 141. When carrier body 141 is substantially constrained against movement by a stereotactic system (e.g., stereotactic frame 52), drive mechanism 144 may be used to establish implantable lead 116 in a rotational orientation relative to the stereotactic system.

Figure 4:
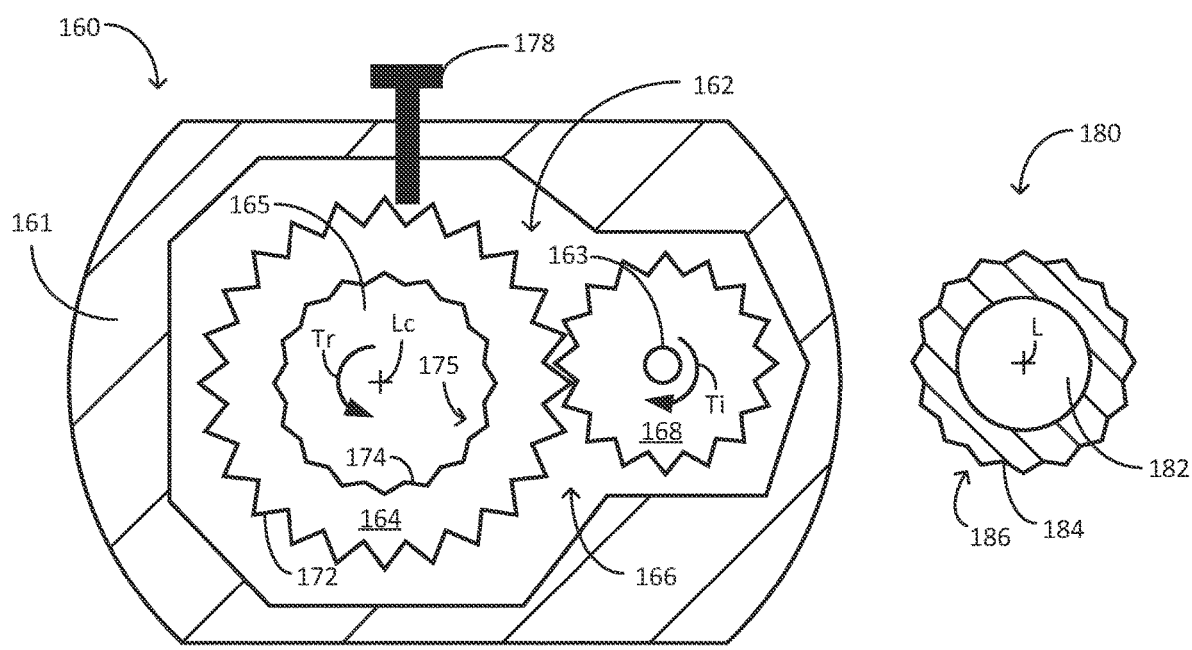
FIG. 4 is a plan view with selected cross-sections illustrating an example drive mechanism.

FIG. 4 illustrates a cross-section of a carrier 160 configured to engage a lead delivery device 180. FIG. 4 illustrates the cross-section of a carrier 160 taken with a cutting plane perpendicular to carrier axis Lc. In FIG. 4, carrier axis Lc is perpendicular to the page. Carrier 160 is an example of carrier 110. Carrier 160 includes carrier body 161, carrier channel 165, drive mechanism 162, torque member 163, gear set 166 including driven gear 164 and driver gear 168, and turn enable 178, which may be configured individually and with reference to each other in the same manner as the like-named components of carrier 110. FIG. 4 also illustrates the cross-section of a lead delivery device 180 taken with a cutting plane perpendicular to longitudinal axis L. In FIG. 4, longitudinal axis L is perpendicular to the page. Lead delivery device 180 is an example of lead delivery device 102. Lead delivery device 180 defines lumen 182 and device exterior surface 184. Lumen 182 is an example of lumen 118 and device exterior surface 184 is an example of collar exterior surface 130 or cannula exterior surface 155. Longitudinal axis L extends through lumen 182 defined by lead delivery device 180. In FIG. 4, carrier 160 is not engaging lead delivery device 180, however lead delivery device is configured to position within carrier channel 165.

Drive mechanism 162 may be configured to receive an input torque Ti via torque member 163 (e.g., clockwise or anti-clockwise). Torque member 163 may be mechanically coupled to a turn knob (e.g., turn knob 146 (FIG. 2, 3)) accessible from outside of carrier body 161, such that a torque imparted to the turn knob (e.g., by a clinician) generates the input torque Ti on torque member 163. Drive mechanism 162 is configured to transmit at least some portion of the input torque Ti and generate a rotational torque Tr around channel axis Lc extending through carrier channel 165. In examples, drive mechanism 162 generates the rotational torque Tr on a driven gear 164 configured to rotate substantially around channel axis Lc. Drive mechanism 162 may include a gear set 166 configured to receive the input torque Ti and cause the rotational torque Tr around channel axis Lc. Gear set 166 may include a driver gear 168 configured to receive the input torque via torque member 163. In examples, driver gear 168 is configured to mesh with driven gear 164. Gear set 166 may include any type of gear, including spur gears, bevel gears, gear racks, straight gears, helical gears, and other gear types sufficient to transfer a torque. In examples, carrier 160 is configured to position a gear axis of driven gear 164 substantially parallel and/or substantially coincident with channel axis Lc.

Gear set 166 may be configured to establish any gear ratio N1:N2 between driver gear 168 and driven gear 164, with N1 substantially equal to the rotational speed of driver gear 168 and N2 substantially equal to the rotational speed of driven gear 164. In examples, N1 may be less than, substantially equal to, or greater than N2. Drive mechanism 162 may be configured to establish a speed ratio S1:S2 between a turn knob (e.g., turn knob 146 (FIG. 2, 3)) and driven gear 164, with S1 substantially equal to the rotational speed of the turn knob and S2 equal to the rotational speed of driven gear 164. In examples, S1 may be less than, substantially equal to, or greater than S2.

In examples, driven gear 164 includes an outer perimeter 172 ("driven gear outer perimeter 172") and an inner perimeter 174 ("driven gear inner perimeter 174"). Driven gear 164 may be configured to generate the rotational torque Tr on driven gear inner perimeter 174. Drive mechanism 162 may be configured within carrier body 161 such that driven gear inner perimeter 174 surrounds channel axis Lc. In examples, driven gear outer perimeter 172 and driven gear inner perimeter 174 rotate around channel axis Lc. Driven gear inner perimeter 174 may be configured to mechanically couple with a surface of lead delivery device 180, such as collar exterior surface 130 and/or cannula exterior surface 155 (FIG. 2, 3). In examples, driven gear inner perimeter 174 defines a plurality of inner gear teeth 175 ("inner gear teeth 175"). Inner gear teeth 175 may be configured to transfer the rotational torque Tr to device exterior surface 184 of lead delivery device 180. Individual teeth of inner gear teeth 175 may have any shape, including involute, cycloid, trochoid, and other gear teeth shapes.

Drive mechanism 162 includes turn enable 178. Turn enable 178 is configured to control the transmission of the rotational torque Tr from drive mechanism 162 to lead delivery device 180. In examples, turn enable 178 is configured to control a rotation of driven gear 164 around channel axis Lc in response to the input torque Ti. Turn enable 178 may be configured to establish a first position wherein driven gear 164 rotates when drive mechanism 162 receives the input torque Ti and a second position wherein driven gear 164 remains substantially stationary when drive mechanism 162 receives the input torque Ti. In the second position, turn enable 178 may be configured to exert a reaction torque on driven gear 164 equal and opposite to the rotational torque Tr generated by drive mechanism 162. In examples, turn enable 178 may be a member configured to engage driven gear outer perimeter 172 in the second position and displace from driven gear outer perimeter 172 in the first position. In the second position, turn enable 178 may be configured to transmit the rotary torque Tr from driven gear 164 to carrier body 161.

Carrier 160 is configured to receive and engage lead delivery device 180 within carrier channel 165. In examples, longitudinal axis L of lead delivery device 180 is substantially parallel to carrier axis Lc when carrier 160 engages lead delivery device 180 within carrier channel 165. Carrier 160 is configured to impart the rotational torque Tr on device exterior surface 184 when carrier 160 engages lead delivery device 180. The rotational torque Tr imparted to lead delivery device 180 may cause a cannula (e.g., cannula 106 (FIGS. 2, 3)) to rotate around longitudinal axis L relative to carrier body 161.

Driven gear inner perimeter 174 may be configured to engage device exterior surface 184 to transmit the rotational torque Tr to lead delivery device 180. For example, inner gear teeth 175 may be configured to engage device exterior surface 184 and transmit the rotational torque Tr to device exterior surface 184. In examples, device exterior surface 184 defines a plurality of teeth 186 ("device teeth 186") configured to engage inner gear teeth 175 when carrier 160 engages lead delivery device 180. Device teeth 186 may be configured to receive the rotational torque Tr from inner gear teeth 175 to cause a cannula of lead delivery device 180 (e.g., cannula 106 (FIGS. 2, 3)) to rotate around longitudinal axis L. Individual teeth of device teeth 186 may have any shape, including involute, cycloid, trochoid, and other gear teeth shapes.

Figure 5:
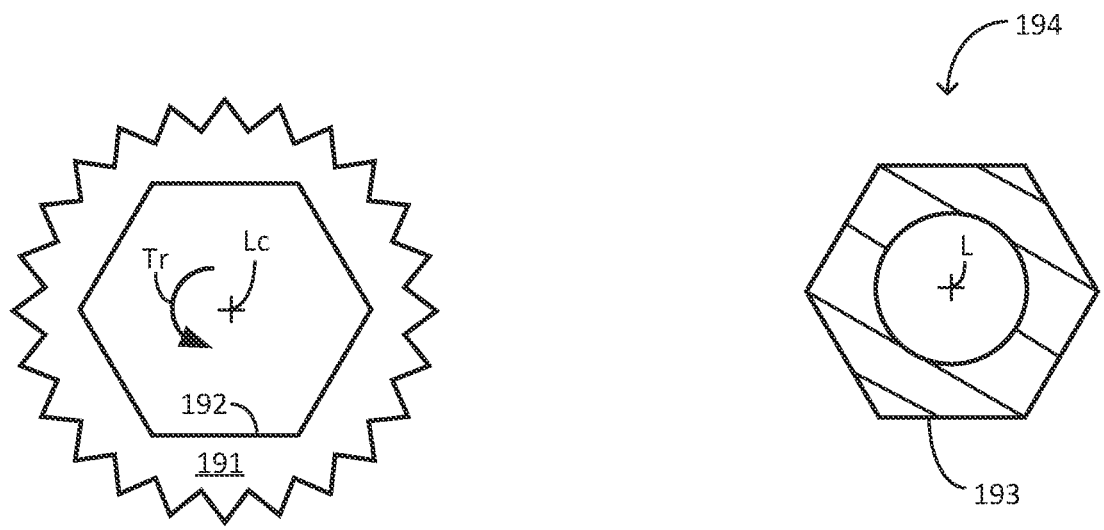
FIG. 5 is a plan view with selected cross-sections illustrating an example driven gear and lead delivery device.
Figure 6:
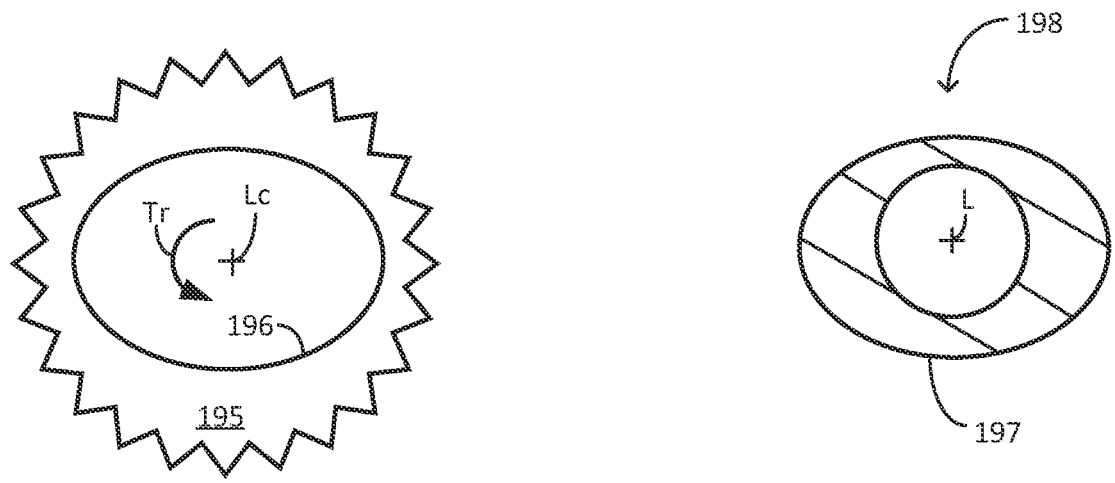
FIG. 6 is a plan view with selected cross-sections illustrating another example driven gear and lead delivery device.

Driven gear 164 may define driven gear inner perimeter 174 to have any shape in the cutting plane of FIG. 4 sufficient to transfer the rotational torque Tr to device exterior surface 184. Device exterior surface 184 may define any shape in the cutting plane of FIG. 4 sufficient to receive the rotational torque from driven gear inner perimeter 174 when carrier 160 engages lead delivery device 180. In examples, driven gear inner perimeter 174 is configured such that rotation of driven gear 164 causes driven gear inner perimeter 174 to contact device exterior surface 184 at one or more contact points and transfer the rotational torque to device exterior surface 184 through the contact points. Device exterior surface 184 may be configured to receive the rotational torque via the contact points from driven gear inner perimeter 174. Driven gear inner perimeter 174 may define a polygon, an oval, a shape curved and/or curvilinear segments, or any other suitable shape. In examples, driven gear inner perimeter 174 is configured such that rotation of driven gear 164 causes driven gear inner perimeter 174 to contact device exterior surface 184 at one or more contact points and transfer the rotational torque to device exterior surface 184 through the contact points. For example, FIG. 5 illustrates a driven gear 191 defining a polygonal shape on a driven gear inner perimeter 192. Driven gear inner perimeter 192 is configured to mechanically engage an exterior surface 193 of lead delivery device 194 and transfer the rotational torque Tr to lead delivery device 194. FIG. 6 illustrates a driven gear 195 defining an oval shape on a driven gear inner perimeter 196. Driven gear inner perimeter 196 is configured to mechanically engage an exterior surface 197 of lead delivery device 198 and transfer the rotational torque Tr to lead delivery device 198. Driven gear 191, 195, driven gear inner perimeter 192, 196, exterior surface 193, 197, and lead delivery device 194, 198 are an examples of driven gear 152, 164, driven gear inner perimeter 174, exterior surface 184, and lead delivery device 102, 180 respectively.

In some examples, driven gear outer perimeter 172 (FIG. 4) may be configured to mechanically engage exterior surface 184, 193, 197 to transfer the rotational torque Tr to lead delivery device 102, 180, 194, 198. For example, carrier 110, 160 may be configured such that a gear axis of driven gear 152, 164, 191, 195 is displaced from channel axis Lc. Carrier 110, 160 may be configured such that the gear axis of driven gear 152, 164, 191, 195 is displaced from carrier channel 142, 165. In examples, when gear axis of driven gear 152, 164, 191, 195 is displaced from carrier channel 142, 165, at least a portion of a pitch diameter of driven gear 152, 164, 191, 195 is within carrier channel 142, 165.

As discussed, cannula 106 (FIGS. 2, 3) is configured to cause a rotation of implantable lead 116 around longitudinal axis L when cannula 106 rotates around longitudinal axis L (e.g., when drive mechanism 144, 160 transfers the rotational torque Tr to stereotactic collar 104 and/or cannula 106). Cannula 106 may be configured to cause implantable lead 116 to rotate synchronously with cannula 106. In examples, cannula 106 includes an inner surface 119 ("cannula inner surface 119") defining a portion of lumen 118 and configured to cause implantable lead 116 to rotate when cannula 106 rotates. Cannula inner surface 119 may define a first shape in a cutting plane perpendicular to longitudinal axis L configured to transfer the rotational torque Tr to implantable lead 116. In examples, implantable lead 116 includes an exterior surface 121 ("lead exterior surface 121") configured to receive the rotational torque Tr from cannula 106. Lead exterior surface 121 may define a second shape in the cutting plane perpendicular to longitudinal axis L configured to cause cannula inner surface 119 to mechanically engage lead exterior surface 121 to transfer the rotational torque Tr from cannula inner surface 119 to lead exterior surface 121.

Figure 7:
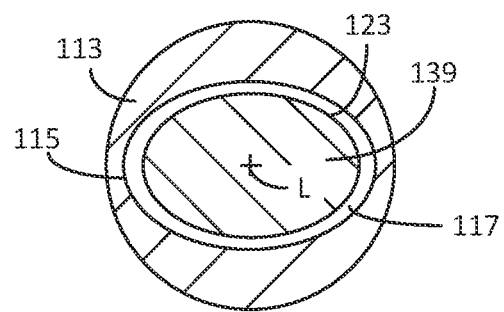
FIG. 7 is a plan view with selected cross-sections illustrating an example cannula and implantable lead.

As an example, FIG. 7 illustrates a cross-section of a cannula 113 and an implantable lead 139 in a cutting plane represented by A-A' in FIG. 3. Cannula 113 includes cannula inner surface 115 defining lumen 117. Implantable lead 139 includes lead exterior surface 123. Longitudinal axis L (perpendicular to the page) extends through implantable lead 139 and lumen 117. Cannula 113, cannula inner surface 115, lumen 117, implantable lead 139 and lead exterior surface 123 are examples of cannula 106, cannula inner surface 119, lumen 118, implantable lead 116 and lead exterior surface 121. In FIG. 7, cannula inner surface 115 defines a substantially elliptical shape having a major axis greater than a minor axis. Lead exterior surface 123 defines a shape (e.g., an ellipse) configured to cause cannula inner surface 115 to mechanically engage lead exterior surface 123 and transfer a rotational torque to lead exterior surface 123 when cannula 113 rotates around longitudinal axis L. In examples, lead exterior surface 123 is configured such that rotation of cannula 113 causes cannula inner surface 115 to contact lead exterior surface 123 at one or more contact points and transfer the rotational torque to lead exterior surface 123 through the contact points. Cannula inner surface 115 may define any cross-sectional shape perpendicular to longitudinal axis L sufficient to transfer a rotational torque to lead exterior surface 123, including elliptical, oval shaped, polygonal, curvilinear, or other appropriate shapes. Lead exterior surface 123 may define any cross-sectional shape perpendicular to longitudinal axis L sufficient to receive the rotational torque from lead exterior surface 123.

Figure 8:
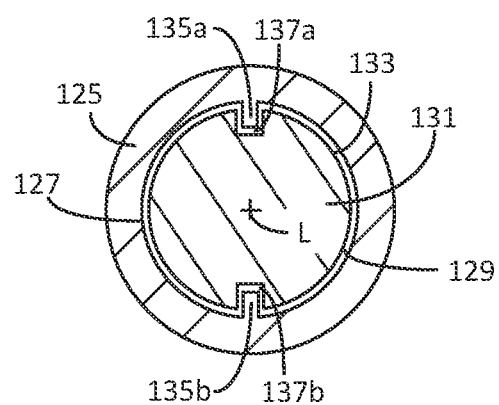
FIG. 8 is a plan view with selected cross-sections illustrating another example cannula and implantable lead.

FIG. 8 illustrates a cross-section of a cannula 125 and an implantable lead 131 in the cutting plane represented by A-A' in FIG. 3. Cannula 125 includes cannula inner surface 127 defining lumen 129. Implantable lead 131 includes lead exterior surface 133. Longitudinal axis L (perpendicular to the page) extends through implantable lead 131 and lumen 129. Cannula 125, cannula inner surface 127, lumen 129, implantable lead 131 and lead exterior surface 133 are examples of cannula 106, cannula inner surface 119, lumen 118, implantable lead 116 and lead exterior surface 121 respectively. In FIG. 8, cannula inner surface 127 defines a protrusion 135a, 135b and lead exterior surface 133 defines a recess 137a, 137b configured to receive protrusion 135a, 135b. Cannula inner surface 127 may define any number of protrusions and lead exterior surface 133 may define any number of recesses. Cannula 125 is translatable substantially parallel to longitudinal axis L when recess 137a, 137b receives the protrusion 135a, 135b. For example, protrusion 135a, 135b may define a ridge substantially parallel to longitudinal axis L, and recess 137a, 137b may define a slot substantially parallel to longitudinal axis L and configured to receive the ridge. In some examples, lead exterior surface 133 defines the protrusion and cannula inner surface 127 defines the recess. Cannula 125 and implantable lead 131 may be configured such that when the recess receives the protrusion, rotation of cannula 125 causes cannula inner surface 127 to contact lead exterior surface 133 at one or more contact points and transfer the rotational torque to lead exterior surface 133 through the contact points.

In some examples, medical device system 10 (FIGS. 2, 3) includes an adjustable mechanism configured to cause implantable lead 116 to rotate substantially synchronously with cannula 106 in a first position and configured to allow substantially independent rotational movement of cannula 106 and implantable lead 116 in a second position. The adjustable mechanism may be, for example, a Touhy-Borst device or a depth stop. The adjustable mechanism may be configured to allow a clinician to select the first position or the second position, and/or manipulate the adjustable mechanism from the first position to the second position, and vice-versa.

Figure 9:
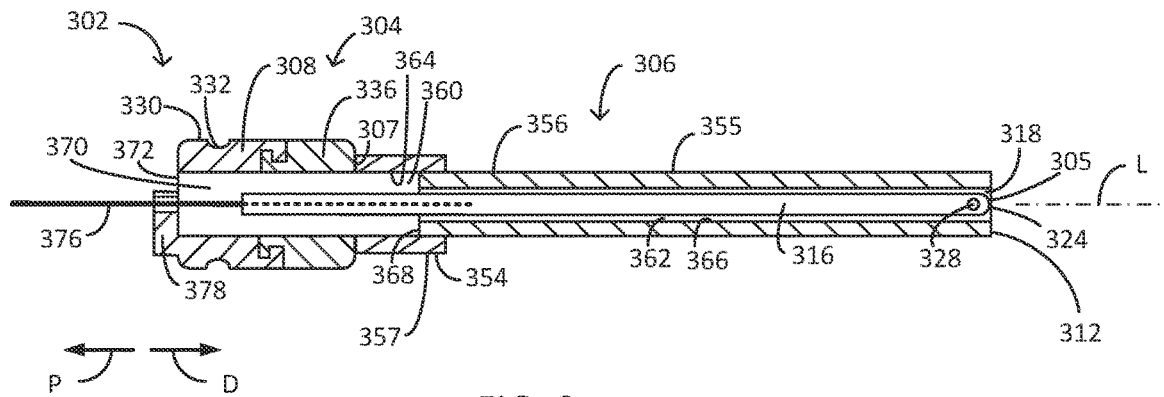
FIG. 9 is a plan view with selected cross-sections illustrating an example lead delivery device.
Figure 10:
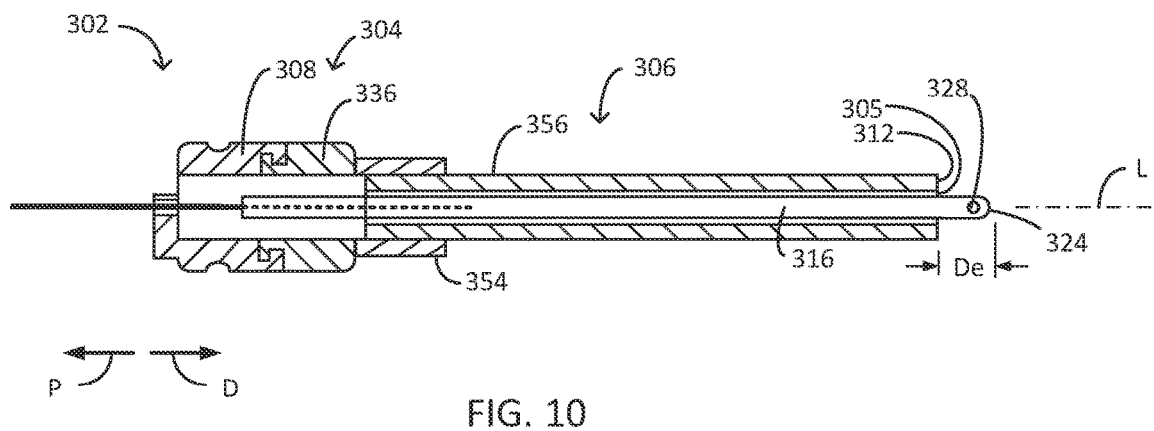
FIG. 10 is a plan view with selected cross-sections illustrating the example lead delivery device of FIG. 9 in an example configuration.
Figure 11:
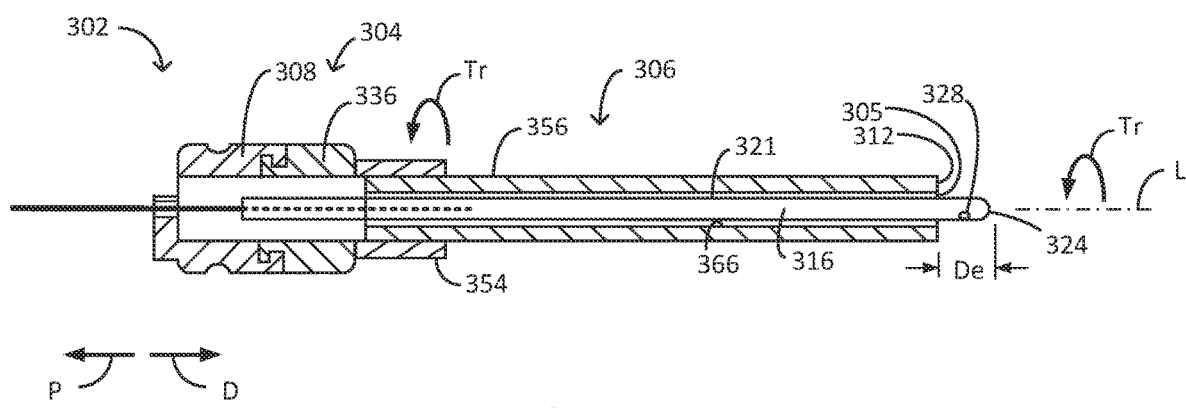
FIG. 11 is a plan view with selected cross-sections illustrating the example lead delivery device of FIG. 9 receiving a rotational torque.

FIGS. 9-11 schematically illustrate a lead delivery device 302 with a translation of a cannula 306 relative to an implantable lead 316, and rotation of cannula 306 and implantable lead 316. Lead delivery device 302 includes stereotactic collar 304 including drive lock ring 308 and drive turn ring 336, cannula 306 including cannula proximal end 307, cannula proximal section 354, and cannula distal section 356, device distal end 312 defining distal opening 305, implantable lead 316, lumen 318, lead distal end 324, electrode 328, collar exterior surface 330 defining divot 332, cannula exterior surface 355, stylet 376, and stylet fixation mechanism 378, which may be configured individually and with reference to each other in the same manner as the like-named components of lead delivery device 102, lead delivery device 180, lead delivery device 194, and/or lead delivery device 198. FIGS. 9-11 illustrate drive lock ring 308, drive turn ring 336, cannula proximal section 354, and cannula distal section 356, as cross-sections with a cutting plane taken parallel to the page along longitudinal axis L. Lead delivery device 302 is an example of lead delivery device 102, 180, 194, 198. Longitudinal axis L extends through lumen 318.

Referring to FIG. 9, lead delivery device 302 is configured to receive a rotational torque Tr from carrier 110, 160 (FIGS. 2-5). In examples, carrier 110, 160 is configured to impart a torque to drive turn ring 336 and/or cannula 306. Cannula 306 is configured to cause implantable lead 316 to rotate around longitudinal axis L when cannula 306 rotates around longitudinal axis L. Cannula 306 is illustrated as including cannula proximal section 354 and cannula distal section 356, although this is not required. As discussed, in examples cannula 306 may be a substantially unitary body between cannula proximal end 307 and device distal end 312.

Lead delivery device 302 is configured such that cannula 306 may translate substantially parallel to longitudinal axis L relative to implantable lead 316. Lead delivery device 302 may be configured such that translation of cannula 306 translates device distal end 312 substantially parallel to longitudinal axis L in the distal direction D and/or proximal direction P relative to lead distal end 324. In examples, cannula distal section 356 may be configured to translate in the distal direction D and/or proximal direction P relative to cannula proximal section 354, such that device distal end 312 translates relative to lead distal end 324. Cannula proximal section 354 may be attached to stereotactic collar 304 (e.g., drive turn ring 336) such that cannula proximal section 354 is substantially constrained from translation independent of stereotactic collar 304.

Cannula distal section 356 may be configured to substantially telescope from cannula proximal section 354. In examples, cannula proximal section 354 defines a proximal lumen 360 and cannula distal section 356 defines a distal lumen 362. An inner surface 364 of cannula proximal section 354 ("proximal inner surface 364") configured to face and surround longitudinal axis L may define proximal lumen 360. An inner surface 366 of cannula distal section 356 ("distal inner surface 366") configured to face and surround longitudinal axis L may define distal lumen 362. Lumen 318 may include proximal lumen 360 and distal lumen 362.

In some examples, as depicted in FIGS. 9-11, a portion of cannula distal section 356 is configured to position within proximal lumen 360. Cannula distal section 356 may be configured to translate within proximal lumen 360 to cause device distal end 312 to translate relative to stereotactic collar 304. In other examples, distal lumen 362 may be configured to surround some portion of cannula proximal section 354, such that cannula distal section 356 translates over a proximal exterior surface 357 to translate device distal end relative to stereotactic collar 304. Further, although cannula distal section 356 is depicted as defining a proximal end 368 ("distal section proximal end 368") within proximal lumen 360 of cannula proximal section 354 in FIG. 9, in examples, distal section proximal end 368 may be located within a channel 370 defined by stereotactic collar 304 ("collar channel 370"). Lumen 318 may include collar channel 370. In some examples, cannula distal section 356 may extend through delivery device access 372, such that distal section proximal end 368 is proximal to delivery device access 372.

FIG. 10 illustrates lead delivery device 302 in a configuration with cannula 306 translated substantially parallel to longitudinal axis L relative to implantable lead 316 (e.g., as a result of withdrawing cannula distal section 356 in the proximal direction P. In FIG. 10, cannula distal section 356 is withdrawn such that lead distal end 324 is distal to device distal end 312 and device distal opening 305 by the displacement De. Electrode 328 is distal to device distal end 312 and device distal opening 305. Relative translation of cannula 306 and implantable lead 316 may be employed to substantially unsheathe electrode 328 when in the vicinity of a target site (e.g., target site 60 (FIG. 1)). Hence, in the configuration depicted in FIG. 10, cannula 306 has substantially uncovered electrode 328 to allow and/or enhance the delivery of therapy and/or record signals/deliver stimulation from electrode 328 to a target site, such as target site 60 (FIG. 1). In FIG. 10, cannula 306 has been caused to translate relative to implantable lead 316 by translating cannula distal section 356 proximally relative to cannula proximal section 354 and stereotactic collar 304, although this is not necessary in all examples. In some examples (e.g., when cannula 306 is a unitary, rigid body), cannula 306 may be caused to translate relative to implantable lead 316 by translating the entirety of cannula 306 relative to implantable lead 316. Stereotactic collar 304 may be configured to translate in the proximal direction P when cannula 306 translates in the proximal direction P, and may be configured to translate in the distal direction D when cannula 306 translates in the distal direction D.

FIG. 11 illustrates lead delivery device 302 receiving a rotational torque Tr as cannula distal section 356 is proximally withdrawn. Lead distal end 324 is distal to device distal end 312 and device distal opening 305 by the displacement De. In FIG. 11, stereotactic collar 304 and/or cannula 306 receives the rotational torque Tr (e.g., from carrier 110, 160 (FIGS. 2-5)). An inner surface of cannula 306 (e.g., distal inner surface 366) mechanically engages lead exterior surface 321 and transfers the rotational torque Tr to lead exterior 321, causing rotation of implantable lead 316 around longitudinal axis L. Rotation of implantable lead 316 causes rotation of electrode 328 around longitudinal axis L. Hence, lead delivery device 302 may be configured to vary the relative orientation of electrode 328 with respect to target site 60 (FIG. 1) in order to identify presence of a biomarker by sensing and/or evaluate an effectiveness of stimulation and/or therapy delivered. When lead delivery device 302 is engaged by carrier 110, 160 (FIGS. 2-5) and carrier 110, 160 is held substantially stationary by stereotactic frame 52 (FIG. 1), lead delivery device 302 may define an angle of rotation corresponding to the relative orientation of electrode 328 evaluated. The defined angle of rotation and translation of each relative orientation of electrode 328 may be recorded, such that the clinician may repeat a relative orientation of electrode 328 deemed effective.

As previously discussed, lead delivery device 302 may cause rotation of implantable lead 316 around longitudinal axis L when lead distal end 324 is proximal to or substantially even with device distal end 312 and device distal opening 305 (e.g., as shown in FIG. 9). With lead distal end 324 proximal to or substantially even with device distal end 312 and device distal opening 305, inner surface of cannula 306 (e.g., distal inner surface 366) may mechanically engage lead exterior surface 321 and transfer a torque (e.g., a torque around longitudinal axis L) to lead exterior 321, causing rotation of implantable lead 316 and electrode 328 around longitudinal axis L.

In examples, lead delivery device 302 is configured to engage a stylet 376 (FIG. 9) configured to transmit a force substantially parallel to longitudinal axis L to implantable lead 316. Stylet 376 may be configured to transmit the force in the distal direction D and/or the proximal direction P. In examples, stylet 376 is an elongated member extending into implantable lead 316. Implantable lead 316 may be configured such that a force imparted by stylet 376 in the distal direction D causes implantable lead 316 to translate relative to cannula 306 in the distal direction D. Implantable lead 316 may be configured such that a force imparted by stylet 376 in the proximal direction P causes implantable lead 316 to translate relative to cannula 306 in the proximal direction P. Similarly, implantable lead 316 may be configured such that translation of stylet 376 relative to stereotactic collar 304 and/or cannula 306 causes a translation of implantable lead 316 relative to stereotactic collar 304 and/or cannula 306. Implantable lead 316 may be configured such when stylet 376 is substantially stationary with respect to stereotactic collar 304 and/or cannula 306, stylet 376 maintains implantable lead 316 substantially stationary to stereotactic collar 304 and/or cannula 306. In examples, stylet 376 may be configured to rotate around longitudinal axis L when stereotactic collar 304 rotates around longitudinal axis L. Stereotactic collar 304 may be configured to impart a torque around longitudinal axis L to stylet 376. For example, one of stylet 376 or stereotactic collar 304 may include a protrusion and the other of stylet 376 or stereotactic collar 304 may include a recess configured to receive the protrusion. Stylet 376 may be configured such that a torque on the protrusion and/or recess imparts a torque to stylet 376.

Lead delivery device 302 (e.g., stereotactic collar 304) may include stylet fixation mechanism 378 configured to resist a translation of stylet 376 relative to stereotactic collar 304 and/or cannula 306. Stylet fixation mechanism 378 may include, for example, a snap-lock configured to resist translation of stylet fixation mechanism 378 relative to stereotactic collar 304 and/or cannula 306. In examples, stylet fixation mechanism 378 is configured to index a plurality of linear displacements of stylet 376 (e.g., displacements substantially parallel to longitudinal axis L). Stylet 376 may be configured to cause stylet fixation mechanism 378 to resist the translation of stylet 376 at predetermined points on stylet 376. Stylet 376 may be configured to overcome the resistance using, e.g., a greater force on stylet 376, repositioning of stylet 376 relative to stylet fixation mechanism 378, repositioning of stylet fixation mechanism 378 relative to stylet 376, or some other method. In examples, stylet 376 includes a plurality of indentations along a longitudinal axis of stylet 376, where each indentation is configured to interact with a protrusion of stylet fixation mechanism 378 as stylet 376 translates linearly through stylet fixation mechanism 378. The protrusion of stylet fixation mechanism 378 may be configured to resist further translation of stylet 376 as each indentation interacts with the protrusion. Stylet 376 may be configured to overcome the resistance by repositioning stylet 376 and/or stylet fixation mechanism 378 such that the protrusion no longer interacts with the indentation sufficiently to resist the translation of stylet 376. In some examples, stylet fixation mechanism 378 includes a thumb screw or other adjustable mechanism configured to resist the translation of stylet 376 through stylet fixation mechanism 378.

In examples, stylet fixation mechanism 378 may include a rotatable locking collar configured to engage stylet 376. The rotatable locking collar may define an opening configured to allow stylet 376 to pass therethrough. In examples, the rotatable locking collar may have a first position configured to allow linear translation of stylet 376 and a second position configured to resist further translation of stylet 376. The rotatable locking collar may be configured to such that a clinician may adjust the rotatable locking collar between the first position and the second position, or other positions which may be defined by the rotatable locking collar.

Figure 12:
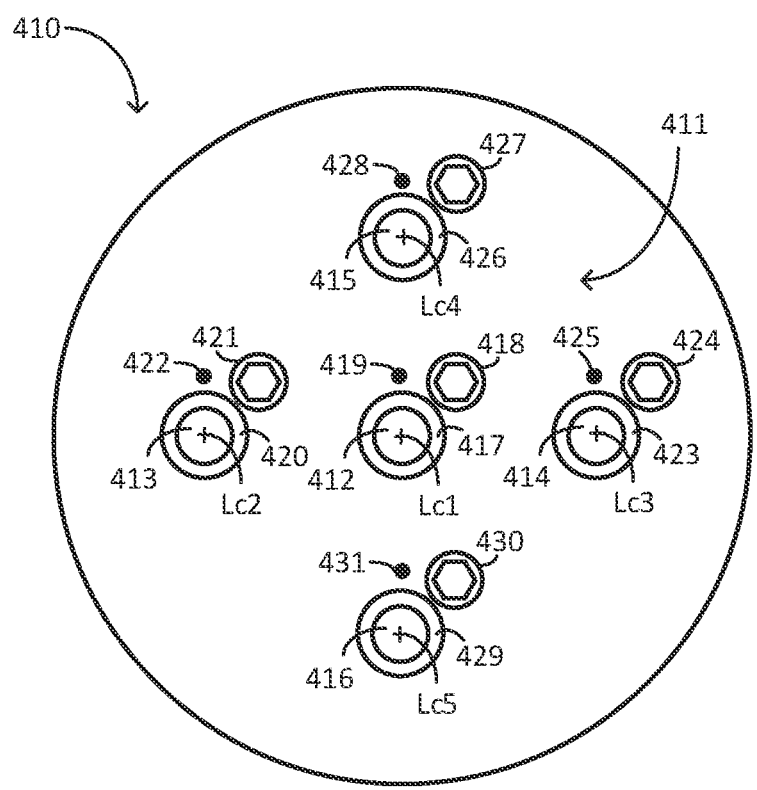
FIG. 12 is a plan view illustrating an example carrier defining a plurality of channels.

FIG. 12 schematically illustrates a carrier 410 defining a plurality of carrier channels 411 including carrier channel 412 defining carrier axis Lc1, carrier channel 413 defining carrier axis Lc2, carrier channel 414 defining carrier axis Lc3, carrier channel 415 defining carrier axis Lc4, and carrier channel 416 defining carrier Lc5. In examples, each of carrier axis Lc1, Lc2, Lc3, Lc4, Lc5 is substantially parallel to every other of carrier axis Lc1, Lc2, Lc3, Lc4, Lc5. The plurality of carrier channels 411 may include any number of carrier channels and may define any pattern on carrier 410. In examples, each of carrier channels 412, 413, 414, 415, 416 is configured to define one of an anterior, posterior, medial, or lateral direction relative to a target site (e.g., target site 60 (FIG. 1)). Plurality of carrier channels 411 may include additional carrier channels configured to define additional directions, such as anterio-medial, anterio-lateral, posterior-medial, and/or posterior-lateral. In examples, carrier 410 is configured to be rotatable around one or more of Lc1, Lc2, Lc3, Lc4, Lc5 to vary the relative locations of carrier channels 412, 413, 414, 415, 416. For example, carrier 410 may be rotatable around Lc1 to convert a "+" configuration (as depicted in FIG. 12) to an "X" configuration. Additional parallel channels may be in a M×N matrix (square/rectangular) configuration either equidistant or non-equidistant from the carrier channel 412.

Each of carrier channel 412, 413, 414, 415, 416 is configured to receive a portion of lead delivery device 102, 302 and engage lead delivery device 102, 302. Carrier 410 may be configured to allow a clinician to insert lead delivery device 102, 302 into one of carrier channel 412, 413, 414, 415, 416 to evaluate a placement of electrode 128, 328 relative to a target site (target site 60 (FIG. 1)). If desired (e.g., based on the evaluation), the clinician may withdraw lead delivery device 102, 302 and insert lead delivery device 102, 302 into another of carrier channel 412, 413, 414, 415, 416 and/or evaluate two or multiple channels simultaneously as deemed necessary.

Carrier 410 includes a plurality of drive mechanisms, with each drive mechanism configured to impart a torque on a lead delivery device extending through one of the channels in the plurality of channels 411. For example, carrier channel 412 includes a drive mechanism including driven gear 417, turn knob 418, and turn enable 419. Carrier channel 413 includes a drive mechanism including driven gear 420, turn knob 421, and turn enable 422. Carrier channel 414 includes a drive mechanism including driven gear 423, turn knob 424, and turn enable 425. Carrier channel 415 includes a drive mechanism including driven gear 426, turn knob 427, and turn enable 428. Carrier channel 416 includes a drive mechanism including driven gear 429, turn knob 430, and turn enable 431. Carrier 410 is an example of carrier 110 and/or carrier 160. Carrier channel 412, 413, 414, 415, 416 is an example of carrier channel 142 and/or carrier channel 165. Driven gear 417, 420, 423, 426, 429 is an example of driven gear 152, driven gear 164, driven gear 191, and/or driven gear 195. Turn knob 418, 421, 424, 427, 430 is an example of turn knob 146. Turn enable 419, 422, 425, 428, 431 is an example of turn enable 149 and/or turn enable 178.

Figure 13:
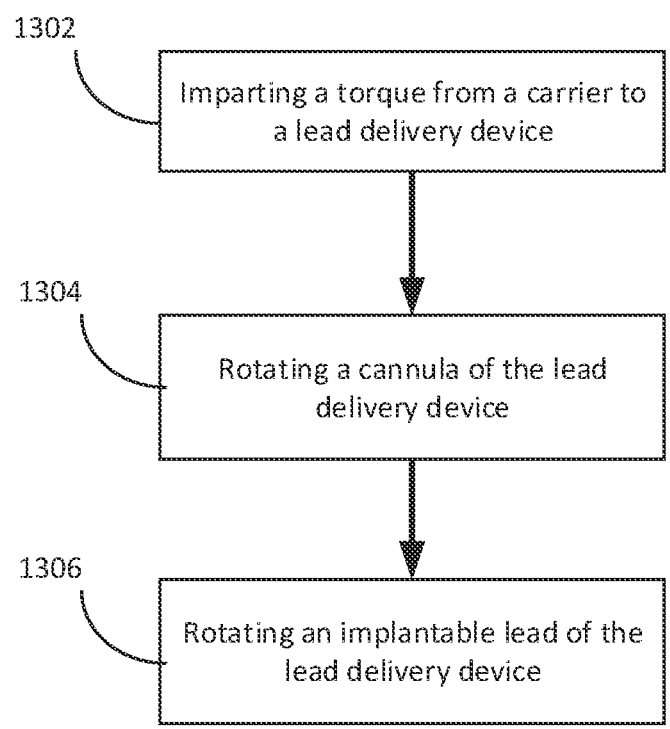
FIG. 13 illustrates an example technique for positioning an implantable lead.

A technique for positioning an implantable lead is illustrated in FIG. 13. Although the technique is described mainly with reference to implantable medical delivery system 100 of FIGS. 2-12, the technique may be applied to other medical delivery systems in other examples.

The technique may include positioning an implantable lead implantable lead 116, 131, 139 within a lumen 118, 117, 129, 318 of a lead delivery device 102, 194, 198, 302 in the vicinity of a target site 60 within a patient using stereotactic system 50. The technique may include positioning a device distal end 112, 312 of lead delivery device 102, 194, 198, 302 in the vicinity of target site 60. In examples, the technique includes positioning an electrode 128, 328 of implantable lead 116, 131, 139 in the vicinity of a target site 60. The technique may include causing implantable lead 116, 131, 139 to translate when stereotactic system 50 causes lead delivery device 102, 194, 198, 302 translate using a stylet 176, 376 engaged with implantable lead 116, 131, 139 and a stereotactic collar 104, 304 of lead delivery device 102, 194, 198, 302.

In examples, the technique includes engaging a carrier 110, 160, 410 with stereotactic system 50 such that a carrier body 141, 161 of carrier 110, 160, 410 is substantially stationary with respect to a portion of stereotactic system 50. The technique may include inserting a portion of lead delivery device 102, 194, 198, 302 within a carrier channel 142, 165 defined by carrier 110, 160, 410. In examples, the technique includes positioning a stereotactic collar 104, 304 of lead delivery device 102, 194, 198, 302 within carrier channel 142, 165. The technique may include causing a carrier 110, 160, 410 to engage lead delivery device 102, 194, 198, 302 within carrier channel 142, 165.

The technique may include translating a cannula 106, 306 of lead delivery device 102, 194, 198, 302 relative to implantable lead 116, 131, 139. The technique may include translating cannula 106, 306 in a direction substantially parallel to a longitudinal axis L of lead delivery device 102, 194, 198, 302. In examples, the technique includes translating cannula 106, 306 relative to implantable lead 116, 131, 139 such that a lead distal end 124, 324 is distal to a device distal opening 105, 305 defined by lumen 118, 117, 129, 318. The technique may include translating cannula 106, 306 relative to implantable lead 116, 131, 139 such that electrode 128, 328 is distal to a device distal opening 105, 305. In examples, the technique includes translating cannula 106, 306 relative to implantable lead 116, 131, 139 such that a lead distal end 124, 324 and/or electrode 128, 328 is proximal or substantially even with device distal opening 105, 305. In some examples, translating cannula 106, 306 relative to implantable lead 116, 131, 139 includes translating a cannula distal section 156, 356 relative to a cannula proximal section 154, 354. In some examples, translating cannula 106, 306 relative to implantable lead 116, 131, 139 includes translating stereotactic collar 104, 304 when cannula 106, 306 translates.

The technique includes imparting a torque from a carrier 110, 160, 410 to a lead delivery device 102, 194, 198, 302 positioned in a carrier channel 142, 165 of the carrier 110, 160, 410 (1302). In examples, the technique includes imparting the torque to stereotactic collar 104, 304 of lead delivery device 102, 194, 198, 302. The technique may include imparting the torque to a drive turn ring 136, 336 of stereotactic collar 104, 304. In examples, the technique includes imparting the torque to a cannula 106, 306 of lead delivery device 102, 194, 198, 302.

In examples, the technique includes imparting the torque using a drive mechanism 144, 162 of carrier 110, 160, 410. The technique may include supplying an input torque to drive mechanism 144, 162 and generating the imparted torque using the input torque. In examples, the technique includes supplying the input torque to a turn knob 146 of drive mechanism 144, 162. The technique may include adjusting a turn enable 149, 178 of drive mechanism 144, 162 to enable drive mechanism 144, 162 to impart the torque to lead delivery device 102, 194, 198, 302. In examples, the technique includes imparting the torque using a driven gear 152, 164, 191, 196.

The technique may include using a driven gear inner perimeter 174, 192, 196 to impart the torque to lead delivery device 102, 194, 198, 302. The technique may include causing driven gear inner perimeter 174, 192, 196 to contact device exterior surface 184 of lead delivery device 102, 194, 198, 302 at one or more contact points and imparting the torque to device exterior surface 184 through the contact points. The technique may include receiving the imparted torque on device exterior surface 184 via the contact points. In examples, the technique includes using a driven gear outer perimeter 172 to impart the torque to lead delivery device 102, 194, 198, 302.

The technique includes causing a cannula 106, 306 to rotate around a longitudinal axis of lead delivery device 102, 194, 198, 302 using the imparted torque (1304). In examples, the technique includes causing a cannula inner surface 119, 115, 127 defining a lumen 118, 117, 129, 318 to rotate around longitudinal axis L using the rotation of the cannula. The technique includes causing an implantable lead 116, 131, 139 within lumen 118, 117, 129, 318 to rotate around the longitudinal axis L using the rotation of cannula 106, 306 (1306). In examples, the technique includes causing a cannula inner surface 119, 115, 127 to mechanically engage a lead exterior surface 121, 123, 133 of the implantable lead 116, 131, 139. The technique may include causing cannula inner surface 119, 115, 127 to contact lead exterior surface 121, 123, 133 at one or more contact points and transmitting the torque to lead exterior surface 121, 123, 133 through the contact points. The technique may include receiving the torque on lead exterior surface 121, 123, 133 via the contact points.

The technique may include recording a rotational orientation of implantable lead 116, 131, 139 relative to carrier body 141, 161 and/or stereotactic system 50. In examples, the technique includes varying the rotational position of implantable lead 116, 131, 139 when electrode 128, 328 is distal or proximal to device distal opening 105, 305 and/or when both are aligned. The technique may include removing lead delivery device 102, 194, 198, 302 from one of carrier channel 412, 413, 414, 415, 416 and inserting lead delivery device 102, 194, 198, 302 into another of carrier channel 412, 413, 414, 415, 416. The technique may include simultaneous use of two or more carrier channels in the plurality of carrier channels 412, 413, 414, 415, 416 by the clinician. For example, the technique may include placing a first lead delivery device in a first carrier channel and a second lead delivery device in a second carrier channel. The technique may include placing a lead delivery device in any number of carrier channels sequentially or simultaneously as deemed necessary by the clinician.

The present disclosure includes the following examples:

Example 1: A medical delivery system comprising: a lead delivery device defining a longitudinal axis and a lumen, wherein the lead delivery device comprises: a stereotactic collar defining a collar access at a proximal end of the lead delivery device; and a cannula attached to the stereotactic collar and defining a distal opening at a distal end of the lead delivery device, wherein the lumen extends from the collar access to the distal opening, wherein the cannula is configured to engage an implantable lead within the lumen, wherein the cannula is configured to rotate the implantable lead around the longitudinal axis when the cannula rotates around the longitudinal axis, and wherein the cannula is configured to translate substantially parallel to the longitudinal axis relative to the implantable lead; and a carrier configured to engage the lead delivery device, wherein the carrier defines a carrier body, and wherein the carrier comprises a drive mechanism configured to impart a torque to the lead delivery device to cause the cannula to rotate around the longitudinal axis relative to the carrier body when the carrier engages the lead delivery device.

Example 2: The medical delivery system of example 1, wherein the carrier defines a carrier channel, and wherein a portion of the lead delivery device is configured to insert into the carrier channel when the carrier engages the lead delivery device.

Example 3: The medical delivery device of example 1 or 2, wherein the carrier is configured to limit translation of the stereotactic collar in a direction substantially parallel to the longitudinal axis when the drive mechanism imparts the torque to the lead delivery device.

Example 4: The medical delivery device of any combination of examples 1-3, wherein the longitudinal axis intersects the collar access and the distal opening.

Example 5: The medical delivery device of any combination of examples 1-4, wherein the drive mechanism includes a turn knob configured to receive an input torque, wherein the turn knob is accessible from an exterior surface of the carrier, and wherein the drive mechanism is configured impart the torque to the lead delivery device using the input torque.

Example 6: The medical delivery device of example 5, further comprising the implantable lead, wherein the implantable lead includes a directional electrode configured to rotate about the longitudinal axis when the implantable lead rotates about the longitudinal axis, and wherein the lead delivery device is configured to translate the cannula from a first position wherein the distal opening is distal to the electrode to a second position wherein the distal opening is proximal to the electrode.

Example 7: The medical delivery device of any combination of examples 1-6, wherein the carrier is configured to indicate an angle of rotation of the cannula with respect to the carrier.

Example 8: The medical delivery device of any combination of examples 1-7, wherein the stereotactic collar comprises: a drive turn ring attached to a drive lock ring, wherein the drive turn ring is configured to rotate around the longitudinal axis relative to the drive lock ring when the drive mechanism imparts the torque to the lead delivery device, and wherein the cannula is rotationally coupled to the drive turn ring.

Example 9: The medical delivery device of any combination of examples 1-8, wherein the cannula comprises: a proximal section attached to the stereotactic collar; a distal section comprising the distal end of the lead delivery device, wherein the distal section is configured to translate substantially parallel to the longitudinal axis relative to the proximal section, wherein the proximal section and the distal section are configured to rotate around the longitudinal axis when the cannula rotates around the longitudinal axis, and wherein the lumen extends through the proximal section and the distal section.

Example 10: The medical delivery device of any combination of examples 1-9, wherein: the carrier defines an access port and an outlet port and a carrier channel extending between the access port and the outlet port, the stereotactic collar is configured to position between the access port and the outlet port when the carrier engages the lead delivery device, the cannula is configured to extend through the outlet port when the carrier engages the lead delivery device, and the longitudinal axis extends through the access port and the outlet port when the carrier engages the lead delivery device.

Example 11: The medical delivery device of any combination of examples 1-10, wherein the drive mechanism comprises: a driven gear configured to mechanically engage the lead delivery device to impart the torque to the lead delivery device.

Example 12: The medical delivery device of any combination of examples 1-11, further comprising a stylet configured to translate relative to the stereotactic collar, wherein the stylet is configured to translate the implantable lead substantially parallel to the longitudinal axis relative to the cannula when the stylet translates relative to the stereotactic collar.

Example 13: The medical delivery device of example 12, wherein the stereotactic collar includes a stylet fixation mechanism configured to limit a translation of the stylet relative to the stereotactic collar.

Example 14: The medical delivery device of any combination of examples 1-13, wherein the drive mechanism comprises: a turn enable having a first position and a second position, wherein the turn enable is configured to allow the drive mechanism to impart the torque to the lead delivery device in the first position and configured to prevent the prevent the drive mechanism from imparting the torque to the lead delivery device in the second position.

Example 15: A medical delivery system comprising: a lead delivery device having a proximal end and a distal end defining a longitudinal axis and a lumen, wherein the lead delivery device comprises: a stereotactic collar defining a collar access at a proximal end of the lead delivery device; and a cannula attached to the stereotactic collar and defining a distal opening at a distal end of the lead delivery device, wherein the lumen extends from the collar access to the distal opening, wherein the cannula is configured to engage an implantable lead within the lumen, wherein the cannula is configured to rotate the implantable lead around the longitudinal axis when the cannula rotates around the longitudinal axis, and wherein the cannula is configured to translate substantially parallel to the longitudinal axis relative to the implantable lead; and a carrier configured to engage the lead delivery device, wherein the carrier defines a carrier body, wherein the carrier comprises: a drive mechanism configured to receive a torque and impart a portion of the torque to the lead delivery device to cause the cannula to rotate around the longitudinal axis relative to the carrier body when the carrier engages the lead delivery device, and wherein the drive mechanism comprises: a turn knob configured to receive the torque, wherein the turn knob is accessible from an exterior surface of the carrier; and a turn enable having a first position and a second position, wherein the turn enable is configured to allow the drive mechanism to impart the portion of the torque to the lead delivery device in the first position and configured to prevent the prevent the drive mechanism from imparting the portion of the torque to the lead delivery device in the second position.

Example 16: The medical delivery device of example 15, wherein the carrier is configured to indicate an angle of rotation of the cannula with respect to the carrier.

Example 17: The medical delivery device of example 15 or 16, further comprising a stylet configured to translate the implantable lead relative to the cannula when the stylet translates relative to the stereotactic collar, and wherein the stereotactic collar includes a stylet fixation mechanism configured to limit the translation of the stylet relative to the stereotactic collar.

Example 18: The medical delivery device of any combination of examples 15-17, wherein: the carrier defines a plurality of carrier channels and plurality of drive mechanisms, a portion of the lead delivery device is configured to insert into each carrier channel in the plurality of carrier channels, and the carrier is configured such that, when the lead delivery device inserts into one of the carrier channels, an individual drive mechanism in the plurality of drive mechanisms is configured to receive an individual torque and impart a portion of the individual torque to the lead delivery device, wherein the individual drive mechanism comprises: an individual turn knob configured to receive the individual torque, wherein the individual turn knob is accessible from an exterior surface of the carrier; and an individual turn enable having a primary position and a secondary position, wherein the individual turn enable is configured to allow the drive mechanism to impart the portion of the torque to the lead delivery device in the primary position and configured to prevent the prevent the drive mechanism from imparting the portion of the torque to the lead delivery device in the secondary position.

Example 19: A method comprising: imparting a torque from a drive mechanism of a carrier to a lead delivery device positioned in a carrier channel defined by the carrier; causing a cannula attached to a stereotactic collar of the lead delivery device to rotate around a longitudinal axis of the lead delivery device using the imparted torque; and causing an lumen of the lead delivery device configured to engage an implantable lead to rotate around the longitudinal axis of the lead delivery device using the rotation of the cannula.

Example 20: The method of claim 19, further comprising translating the cannula substantially parallel to the longitudinal axis relative to a stereotactic collar of the lead delivery device.

Various examples of the disclosure have been described. Any combination of the described systems, operations, or functions is contemplated. These and other examples are within the scope of the following claims.

What is claimed is:

1. A medical delivery system for rotating an implantable lead, the medical delivery system comprising:
a lead delivery device defining a longitudinal axis and a lumen, wherein the lead delivery device comprises:
a stereotactic collar defining a collar access at a proximal end of the lead delivery device; and
a cannula attached to the stereotactic collar and defining a distal opening at a distal end of the lead delivery device, the lumen extending from the collar access to the distal opening,
wherein the stereotactic collar is configured to rotate about the longitudinal axis,
wherein the stereotactic collar is configured to cause a rotation of the cannula about the longitudinal axis when the stereotactic collar rotates about the longitudinal axis,
wherein an inner surface of the cannula is configured to engage an exterior surface of the implantable lead when the implantable lead extends within the lumen and the stereotactic collar causes the rotation of the cannula, the inner surface configured such that the engagement causes a synchronous rotation of the implantable lead with the cannula about the longitudinal axis
wherein the cannula is configured to translate substantially parallel to the longitudinal axis relative to the implantable lead; and
a carrier configured to engage the lead delivery device, wherein the carrier defines a carrier body, and
wherein the carrier comprises a drive mechanism configured to impart a torque to the lead delivery device to cause the stereotactic collar to rotate relative to the carrier body and about the longitudinal axis when the carrier engages the lead delivery device.

2. The medical delivery system of claim 1, wherein the carrier body defines a carrier channel extending between an access port defined by the carrier body and an outlet port defined by the carrier body, and wherein a portion of the lead delivery device is configured to position within the carrier channel when the carrier engages the lead delivery device.

3. The medical delivery system of claim 1, wherein the carrier is configured to limit translation of the stereotactic collar in a direction substantially parallel to the longitudinal axis when the drive mechanism imparts the torque to the lead delivery device.

4. The medical delivery system of claim 1, wherein the longitudinal axis intersects the collar access and the distal opening.

5. The medical delivery system of claim 1, wherein the drive mechanism includes a turn knob configured to receive an input torque, wherein the turn knob is accessible from an exterior surface of the carrier, and wherein the drive mechanism is configured to impart the torque to the lead delivery device using the input torque.

6. The medical delivery system of claim 5, further comprising the implantable lead, wherein the implantable lead includes a directional electrode configured to rotate about the longitudinal axis when the implantable lead rotates about the longitudinal axis, and wherein the lead delivery device is configured to translate the cannula from a first position wherein the distal opening is distal to the electrode to a second position wherein the distal opening is proximal to the directional electrode.

7. The medical delivery system of claim 1, wherein the carrier is configured to indicate an angle of rotation of the cannula with respect to the carrier.

8. The medical delivery system of claim 1, wherein the stereotactic collar comprises: a drive turn ring attached to a drive lock ring, wherein the drive turn ring is configured to rotate around the longitudinal axis relative to the drive lock ring when the drive mechanism imparts the torque to the lead delivery device, and wherein the cannula is rotationally coupled to the drive turn ring.

9. The medical delivery system of claim 1, wherein the cannula comprises:
a proximal section attached to the stereotactic collar; and
a distal section comprising the distal end of the lead delivery device,
wherein the distal section is configured to translate substantially parallel to the longitudinal axis relative to the proximal section,
wherein the proximal section and the distal section are configured to rotate around the longitudinal axis when the cannula rotates around the longitudinal axis, and
wherein the lumen extends through the proximal section and the distal section.

10. The medical delivery system of claim 1, wherein:
the carrier defines an access port and an outlet port and a carrier channel extending between the access port and the outlet port,
the stereotactic collar is configured to position between the access port and the outlet port when the carrier engages the lead delivery device,
the cannula is configured to extend through the outlet port when the carrier engages the lead delivery device, and
the longitudinal axis extends through the access port and the outlet port when the carrier engages the lead delivery device.

11. The medical delivery system of claim 1 wherein the drive mechanism comprises: a driven gear configured to mechanically engage the lead delivery device to impart the torque to the lead delivery device.

12. The medical delivery system of claim 1, further comprising a stylet configured to translate relative to the stereotactic collar, wherein the stylet is configured to translate the implantable lead substantially parallel to the longitudinal axis relative to the cannula when the stylet translates relative to the stereotactic collar.

13. The medical delivery system of claim 12, wherein the stereotactic collar includes a stylet fixation mechanism configured to limit a translation of the stylet relative to the stereotactic collar.

14. The medical delivery system of claim 1, wherein the drive mechanism comprises: a turn enable having a first position and a second position, wherein the turn enable is configured to allow the drive mechanism to impart the torque to the lead delivery device in the first position and configured to prevent the drive mechanism from imparting the torque to the lead delivery device in the second position.

15. A medical delivery system for rotating an implantable lead, the medical delivery system comprising:
a lead delivery device having a proximal end and a distal end defining a longitudinal axis and a lumen, wherein the lead delivery device comprises:
a stereotactic collar defining a collar access at the proximal end; and
a cannula attached to the stereotactic collar and defining a distal opening at a distal end of the lead delivery device, the lumen extending from the collar access to the distal opening,
wherein the stereotactic collar is configured to rotate about the longitudinal axis,
wherein the stereotactic collar is configured to cause a rotation of the cannula about the longitudinal axis when the stereotactic collar rotates about the longitudinal axis,
wherein an inner surface of the cannula is configured to engage an exterior surface of the implantable lead when the implantable lead extends within the lumen and the stereotactic collar causes the rotation of the cannula, the inner surface configured such that the engagement causes a synchronous rotation of the implantable lead with the cannula about the longitudinal axis
wherein the cannula is configured to translate substantially parallel to the longitudinal axis relative to the implantable lead; and
a carrier configured to engage the lead delivery device,
wherein the carrier defines a carrier body,
wherein the carrier comprises: a drive mechanism configured to receive a torque and impart a portion of the torque to the lead delivery device to cause stereotactic collar to rotate relative to the carrier body and about the longitudinal axis when the carrier engages the lead delivery device, and
wherein the drive mechanism comprises:
a turn knob configured to receive the torque, wherein the turn knob is accessible from an exterior surface of the carrier; and
a turn enable having a first position and a second position, wherein the turn enable is configured to allow the drive mechanism to impart the portion of the torque to the lead delivery device in the first position and configured to prevent the drive mechanism from imparting the portion of the torque to the lead delivery device in the second position.

16. The medical delivery system of claim 15, wherein the carrier is configured to indicate an angle of rotation of the cannula with respect to the carrier.

17. The medical delivery system of claim 15, further comprising a stylet configured to translate the implantable lead relative to the cannula when the stylet translates relative to the stereotactic collar, and wherein the stereotactic collar includes a stylet fixation mechanism configured to limit the translation of the stylet relative to the stereotactic collar.

18. The medical delivery system of claim 15, wherein:
the carrier defines a plurality of carrier channels and plurality of drive mechanisms,
a portion of the lead delivery device is configured to insert into each carrier channel in the plurality of carrier channels, and
the carrier is configured such that, when the lead delivery device inserts into one of the carrier channels, an individual drive mechanism in the plurality of drive mechanisms is configured to receive an individual torque and impart a portion of the individual torque to the lead delivery device, wherein the individual drive mechanism comprises:
an individual turn knob configured to receive the individual torque, wherein the individual turn knob is accessible from an exterior surface of the carrier; and
an individual turn enable having a primary position and a secondary position, wherein the individual turn enable is configured to allow the drive mechanism to impart the portion of the torque to the lead delivery device in the primary position and configured to prevent the drive mechanism from imparting the portion of the torque to the lead delivery device in the secondary position.

19. A method comprising:

engaging, using a carrier, a lead delivery device positioned in a carrier channel defined by the carrier;

imparting a torque from a drive mechanism of the carrier to a stereotactic collar of the lead delivery device, wherein the lead delivery device defines a longitudinal axis and a lumen;

causing, using the torque, a rotation of the stereotactic collar about the longitudinal axis;

causing, using the rotation of the stereotactic collar, a cannula attached to the stereotactic collar of to rotate about the longitudinal axis; and engaging, using an inner surface of the cannula, an exterior surface of an implantable lead extending within the lumen to cause a synchronous rotation of the implantable lead with the cannula about the longitudinal axis.

20. The method of claim 19, further comprising translating the cannula relative to the stereotactic collar and substantially parallel to the longitudinal axis.

* * * * *